United States Patent
Sendzik

(10) Patent No.: US 7,368,572 B2
(45) Date of Patent: May 6, 2008

(54) ACETYLENE DERIVATIVES AS INHIBITORS OF HISTONE DEACETYLASE

(75) Inventor: Martin Sendzik, San Mateo, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 477 days.

(21) Appl. No.: 10/922,119

(22) Filed: Aug. 19, 2004

(65) Prior Publication Data

US 2005/0131018 A1   Jun. 16, 2005

Related U.S. Application Data

(60) Provisional application No. 60/496,638, filed on Aug. 20, 2003.

(51) Int. Cl.
C07D 215/38 (2006.01)
C07D 213/72 (2006.01)
C07D 277/08 (2006.01)
C07D 315/00 (2006.01)

(52) U.S. Cl. .................. 546/153; 546/156; 546/304; 546/143; 548/321.5; 548/326.5; 548/557; 549/424

(58) Field of Classification Search ........... 546/153, 546/156, 304, 143; 548/146, 32, 206, 161, 548/215, 321.5, 326.5, 557; 549/424
See application file for complete search history.

(56) References Cited

U.S. PATENT DOCUMENTS

| | | | |
|---|---|---|---|
| 5,972,978 A | 10/1999 | Andersen et al. | |
| 5,990,109 A | 11/1999 | Chen et al. | |
| 2003/0229084 A1 | 12/2003 | Duan et al. | |
| 2004/0053908 A1 | 3/2004 | Funahashi et al. | |
| 2004/0102634 A1 | 5/2004 | Matsuura et al. | |

FOREIGN PATENT DOCUMENTS

| | | |
|---|---|---|
| EP | 0 514 023 A1 | 4/1992 |
| EP | 0 706 795 A2 | 4/1996 |
| WO | WO94/12461 | 6/1994 |
| WO | WO00/20371 | 4/2000 |
| WO | WO01/14331 A2 | 3/2001 |
| WO | WO01/38322 A1 | 5/2001 |
| WO | WO01/70734 A2 | 9/2001 |
| WO | WO02/06195 A1 | 1/2002 |
| WO | WO02/10137 A2 | 2/2002 |
| WO | WO02/26696 A1 | 4/2002 |
| WO | WO02/30879 A2 | 4/2002 |
| WO | WO03/000194 A2 | 1/2003 |
| WO | WO 03/070691 A1 | 8/2003 |

*Primary Examiner*—D. Margaret Seaman
(74) *Attorney, Agent, or Firm*—Wilson Sonsini Goodrich & Rosati

(57) ABSTRACT

The present invention is directed to certain hydroxamate derivatives that are inhibitors of histone deacetylase and are therefore useful in the treatment of diseases associated with histone deacetylase activity. Pharmaceutical compositions and processes for preparing these compounds are also disclosed.

12 Claims, No Drawings

ACETYLENE DERIVATIVES AS INHIBITORS OF HISTONE DEACETYLASE

CROSS-REFERENCE

This application claims priority under 35 USC 119 to provisional application Ser. No. 60/496,638, filed on Aug. 20, 2003, the disclosure of which is incorporated herein by reference in its entirety.

BACKGROUND OF THE INVENTION

1. Field of the Invention

The present invention is directed to certain acetylene derivatives that are inhibitors of histone deacetylase and are therefore useful in the treatment of diseases associated with histone deacetylase activity. Pharmaceutical compositions and processes for preparing these compounds are also disclosed.

2. State of the Art

Interest in histone deacetylase enzymes (HDACs) as targets for pharmaceutical development has centered on the role of HDACs in regulating genes associated with cell-cycle progression and the development and progression of cancer (reviewed in Kramer et. al. *Trends Endocrinol. Metab.* 12, 294-300, (2001)). Several studies have shown that treatment of various cell lines with HDAC inhibitors leads to hyper acetylation of histone proteins and cell-cycle arrest in late $G_1$ phase or at the $G_2$/M transition. Genes involved in the cell cycle that have been shown to be up regulated by HDAC inhibitors include p21, p27, p53 and cyclin E. Cyclin A and cyclin D have been reported to be down regulated by HDAC inhibitors. In tumor cell lines, several studies have shown that treatment with HDAC inhibitors can lead to growth inhibition, growth arrest, terminal differentiation and/or apoptosis. In vivo studies have demonstrated growth inhibition of tumors and a reduction in tumor metastasis as a result of treatment with HDAC inhibitors.

The clearest link between abnormal HDAC activity and cancer occurs in acute promyelocytic leukemia. In this condition, a chromosomal translocation leads to the fusion of the retinoic acid receptor RARα with the promyelocytic leukemia (PML) or promyelocytic leukemia zinc-finger (PLZF) proteins. Both PML-RARα and PLZF-RARα promote the progression of leukemia by repressing retinoic acid-regulated genes through the abnormal recruitment of SMRT-mSin3-HDAC complex (Lin et. al. *Nature* 391, 811-814 (1998)); Grignani et al. *Nature* 391, 815-818 (1998)). Whereas the PML-RARα form of the disease is treatable with retinoic acid, the PLZF-RARα form is resistant to this treatment. For a patient with the retinoic acid-resistant form of the disease, the addition of the HDAC inhibitor sodium butyrate to the dosing regimen led to complete clinical and cytogenic remission (Warrell et al. *J. Natl. Cancer. Inst.* 90, 1621-1625, (1998)). HDACs have also been associated with Huntington's disease (Steffan, et al., *Nature* 413:739-744, "Histone deacetylase inhibitors arrest polyglutamine-dependent neurodegeneration in *Drosophila*").

In summary, an increase in HDAC activity contributes to the pathology and/or symptomatology of a number of diseases. Accordingly, molecules that inhibit the activity of HDAC are useful as therapeutic agents in the treatment of such diseases.

SUMMARY OF THE INVENTION

In a first aspect, this invention provides a compound of Formula (I):

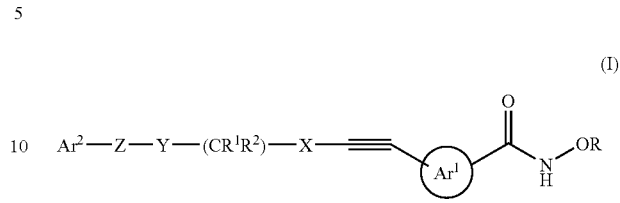

wherein:
R is hydrogen, alkyl, or alkylcarbonyl;
$Ar^1$ is arylene or heteroarylene wherein said $Ar^1$ is optionally substituted with one or two substituents independently selected from alkyl, halo, alkoxy, haloalkoxy, or haloalkyl;
X and Y are independently selected from bond or alkylene wherein alkylene is optionally substituted with halo, haloalkyl, hydroxy, alkoxy, haloalkoxy, amino, alkylamino, or dialkylamino;
$R^1$ is hydrogen or alkyl;
$R^2$ is hydrogen, alkyl, halo, haloalkyl, heteroalkyl, substituted heteroalkyl, aryl, heteroaryl, aralkyl, heteroaralkyl, hydroxyalkyl, alkoxyalkyl, or aminoalkyl; or
$R^1$ and $R^2$ together with the carbon to which they are attached form cycloalkylene or heterocycloalkylene;
Z is —$CONR^3$—, —$NR^4CO$—, —$SO_2NR^5$—, —$NR^6SO_2$—, —$NR^7CONR^8$—, —$NR^9SO_2NR^{10}$—, —$OCONR^{11}$—, or —$NR^{12}COO$— where $R^3$—$R^{12}$ are independently selected from hydrogen, alkyl, hydroxyalkyl, haloalkyl, haloalkoxy, alkoxyalkyl, aralkyl, or heteroaralkyl; and
$Ar^2$ is aryl, aralkyl, aralkenyl, heteroaryl, heteroaralkyl, heteroaralkenyl, heterocycloalkyl, or heterocycloalkylalkyl; and
individual stereoisomers, individual geometric isomers, or mixtures thereof; or a pharmaceutically acceptable salt thereof provided that the hydroxamic acid and the acetylenic groups are not ortho to each other.

In a second aspect, this invention is directed to a pharmaceutical composition comprising a therapeutically effective amount of a compound of Formula (I) or pharmaceutically acceptable salts thereof and a pharmaceutically acceptable excipient.

In a third aspect, this invention is directed to a method for treating a disease in an animal which is mediated by HDAC which method comprises administering to the animal a pharmaceutical composition comprising a therapeutically effective amount of a compound of Formula (I) or a pharmaceutically acceptable salt thereof and a pharmaceutically acceptable excipient. Preferably, the disease is a proliferative disorder such as cancer and bipolar disorders and the animal is human. Preferably, the cancer is prostate cancer, breast cancer, lung melanoma, stomach cancer, neuroblastoma, colon cancer, pancreatic cancer, ovarian cancer, AML, MML, and T-cell lymphoma.

In a fourth aspect, this invention is directed to a method for treating cancer in an animal which method comprises administering to the animal a pharmaceutical composition comprising a therapeutically effective amount of a compound of Formula (I) or a pharmaceutically acceptable salt thereof and a pharmaceutically acceptable excipient in combination with radiation therapy and optionally in combination with one or more compound(s) independently selected from an estrogen receptor modulator, an androgen receptor modulator, retinoid receptor modulator, a cytotoxic agent, another antiproliferative agent, a prenyl-protein transferase inhibitor, an HMG-CoA reductase inhibitor, an HIV protease inhibitor, a reverse transcriptase inhibitor, or an angiogenesis inhibitor. Most preferably, in combination with a retinoid receptor modulator.

In a fifth aspect, this invention is directed to the use of a compound of Formula (I) or a pharmaceutically acceptable salt thereof for the manufacture of a medicament. Preferably, the medicament is useful in the treatment of a disease mediated by HDAC. More preferably, the disease is cancer.

DETAILED DESCRIPTION OF THE INVENTION

Definitions:

Unless otherwise stated, the following terms used in the specification and claims are defined for the purposes of this Application and have the following meanings:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenylene" means a linear divalent hydrocarbon radical of two to six carbon atoms or a branched monovalent hydrocarbon radical of three to six carbon atoms containing one or two double bonds, e.g., ethenylene, propenylene, 2-propenylene, butenylene (including all isomeric forms), and the like.

"Alkylthio" means a —SR radical where R is alkyl as defined above, e.g., methylthio, ethylthio, propylthio (including all isomeric forms), butylthio (including all isomeric forms), and the like.

"Alkylsulfonyl" means a —SO$_2$R radical where R is alkyl as defined above, e.g., methylsulfonyl, ethylsulfonyl, and the like.

"Alkoxycarbonyl" means a —C(O)OR radical where R is alkyl as defined above, e.g., methoxycarbonyl, ethoxycarbonyl, and the like.

"Amino" means a —NH$_2$, or an N-oxide derivative.

"Alkylamino" means a —NHR radical where R is alkyl as defined above, e.g., methylamino, ethylamino, n-, iso-propylamino, n-, iso-, tert-butylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" means a —OR radical where R is alkoxyalkyl as defined above, e.g., methoxyethoxy, 2-ethoxyethoxy, and the like.

"Alkoxyalkyloxyalkyl" means a -(alkylene)-R radical where R is alkoxyalkyloxy as defined above, e.g., methoxyethoxymethyl, 2-ethoxyethoxymethyl, and the like.

"Alkoxycarbonyl" means a —C(O)OR radical where R is alkyl as defined above, e.g., methoxycarbonyl, ethoxycarbonyl, and the like.

"Aminocarbonyl" means a —CONH$_2$ radical.

"Aminoalkyl" means a linear monovalent hydrocarbon radical of one to six carbon atoms, preferably two to six carbon atoms, or a branched monovalent hydrocarbon radical of three to six carbons substituted with at least one, preferably one or two, —NRR' where R is hydrogen, alkyl, or —COR$^a$ where R$^a$ is alkyl, aryl, aralkyl, heteroaryl, or heteroaralkyl, preferably alkyl, optionally substituted phenyl, optionally substituted phenylalkyl, optionally substituted heteroaryl, optionally substituted heteroaralkyl, and R' are independently selected from hydrogen, alkyl, optionally substituted phenyl, optionally substituted phenylalkyl, optionally substituted heteroaryl, optionally substituted heteroaralkyl, or haloalkyl, e.g., aminomethyl, methylaminoethyl, 2-ethylamino-2-methylethyl, 1,3-diaminopropyl, dimethylaminomethyl, diethylaminoethyl, acetylaminopropyl, and the like.

"Aminoalkoxy" means a —OR radical where R is aminoalkyl as defined above, e.g., 2-aminoethoxy, 2-dimethylaminopropoxy, and the like.

"Aryl" means a monovalent monocyclic or bicyclic aromatic hydrocarbon radical of 6 to 12 ring atoms e.g., phenyl, naphthyl or anthracenyl and is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted heteroaryl, cycloalkyloxy, cycloalkenyloxy, optionally substituted phenylcarbonylamino, optionally substituted heteroaryloxy, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)n—R$^a$ (where n is 0 to 2 and R$^a$ is alkyl, haloalkyl, optionally substituted phenyl, optionally substituted phenylalkyl, optionally substituted heteroaryl, or optionally substituted heteroaralkyl), -alkylene-NHSO$^2$—R$^b$ (where R$^b$ is alkyl, haloalkyl, optionally substituted phenyl, optionally substituted phenylalkyl, optionally substituted heteroaryl, optionally substituted heteroaralkyl, or optionally substituted heterocycloalkyl), or -alkylene-NHCO—R$^c$ (where R$^c$ is alkyl, haloalkyl, optionally substituted phenyl, optionally substituted phenylalkyl, optionally substituted heteroaryl, optionally substituted heteroaralkyl, or optionally substituted heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. Preferably, methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, iso-propoxymethyl, or phenoxymethyl. When the aryl ring is divalent it has been referred to as arylene in this application.

"Aralkyl" means a -(alkylene)-R radical where R is aryl as defined above.

"Aralkenyl" means a -alkenylene)-R radical where R is aryl as defined above.

"Cycloalkyl" means a cyclic saturated monovalent hydrocarbon radical of three to ten carbon atoms, e.g., cyclopropyl, cyclobutyl, cyclopentyl, cyclohexyl, or admantyl. The cycloalkyl is optionally substituted with optionally substituted phenyl.

"Cycloalkylene" means a cyclic saturated divalent hydrocarbon radical of three to eight carbon atoms, e.g., cyclopropylene, cyclobutylene, cyclopentylene, or cyclohexylene.

"Cycloalkenyl" means an cyclic unsaturated monovalent hydrocarbon radical of three to six carbon atoms, e.g., cyclopropenyl, cyclobutenyl, cyclohexenyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Cycloalkyloxy" means a —OR radical where R is cycloalkyl as defined above, e.g., cyclopropyloxy, cyclohexyloxy, and the like.

"Cycloalkenyloxy" means a —OR radical where R is cycloalkenyl as defined above, e.g., cyclopropenyloxy, cyclohexenyloxy, and the like.

"Dialkylamino" means a —NRR' radical where R and R' are independently alkyl as defined above, e.g., dimethylamino, diethylamino, methylpropylamino, methylethylamino, n-, iso-, or tert-butylamino, and the like.

"Halo" means fluoro, chloro, bromo, and iodo, preferably fluoro or chloro.

"Haloalkyl" means alkyl as defined herein which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_3$, and the like.

"Haloalkoxy" means a —OR radical where R is haloalkyl as defined above e.g., —OCF$_3$, —OCHF$_2$, and the like.

"Haloalkoxyalkyl" means a -(alkylene)-OR radical where R is haloalkyl as defined above e.g., trifluoromethyloxymethyl, 2,2,2-trifluoroethyloxymethyl, 2-trifluoromethoxyethyl, and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkyloxy" means a —OR radical where R is hydroxyalkyl as defined above.

"Hydroxyalkoxyalkyl" means a -(alkylene)-OR radical where R is hydroxyalkyl as defined above e.g., hydroxymethyloxymethyl, hydroxyethyloxymethyl, and the like.

"Heterocycloalkyl" means a saturated monovalent monocyclic group of 3 to 8 ring atoms in which one or two ring atoms are heteroatoms selected from —N—, —O—, or —S(O)n—, where n is an integer from 0 to 2, the remaining ring atoms being C. More specifically the term heterocycloalkyl includes, but is not limited to, pyrrolidino, piperidino, morpholino, piperazino, tetrahydropyranyl, and thiomorpholino. The heterocycloalkyl ring can optionally contains a keto group within the ring and is optionally substituted with one, two, or three substituents independently selected from alkyl, alkoxy, alkylsulfonyl, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted heteroaryl, cycloalkyloxy, cycloalkenyloxy, optionally substituted phenylcarbonylamino, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)n—R$^a$ (where n is 0 to 2 and R$^a$ is alkyl, haloalkyl, optionally substituted phenyl, optionally substituted phenylalkyl, optionally substituted heteroaryl, or optionally substituted heteroaralkyl), -allene-NHS$_2$—R$^b$ (where R$^b$ is alkyl, haloalkyl, optionally substituted phenyl, optionally substituted phenylalkyl, optionally substituted heteroaryl, or optionally substituted heteroaralkyl), or -alkylene-NHCO—R$^c$ (where R$^c$ is alkyl, haloalkyl, optionally substituted phenyl, optionally substituted phenylalkyl, optionally substituted heteroaryl, or optionally substituted heteroaralkyl) wherein the alkyl chain in haloalkoxyalkyl, optionally substituted phenyloxyalkyl, optionally substituted heteroaryloxyalkyl, or aminoalkyl is optionally substituted with one or two fluoro. Preferably, methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, iso-propoxymethyl, or phenoxymethyl.

"Heterocycloalkylalkyl" means a -(alkylene)-R radical where R is heterocycloalkyl ring as defined above e.g., tetrahydrofuranmethyl, piperazinylmethyl, morpholinylethyl, and the like.

"Heterocycloalkylene" means a saturated divalent cyclic group of 3 to 8 ring atoms in which one or two ring atoms are heteroatoms selected from N, O, or S(O)n, where n is an integer from 0 to 2, the remaining ring atoms being C and optionally containing a keto group within the ring. The heterocycloalkylene ring is optionally substituted with one or two substituents independently selected from alkyl, halo, haloalkyl, hydroxyl, alkoxy and when the heterocycloalkylene is pyrrolidinyl or piperidinyl the nitrogen atom of these rings is optionally substituted, in addition to the substituents listed above, with optionally substituted phenyl, optionally substituted phenylalkyl, optionally substituted heteroaryl, optionally substituted heteroaralkyl, hydroxyalkyl, alkoxyalkyl, or aminoalkyl. Preferably, the heterocycloalkylene is unsubstituted.

"Heteroalkyl" means a linear saturated divalent hydrocarbon radical of one to six carbon atoms or a branched saturated monovalent hydrocarbon radical of three to six carbon atoms wherein one or two carbon atoms have been replaced by a heteroatom independently selected from —CONH—, —NHCO—, —N—, —O— or —S(O)n— where n is 0 to 2. Representative examples include, and are not limited to, —O(CH$_2$)$_2$—, —(CH$_2$)$_2$O—, —CH$_2$O (CH$_2$)$_2$—, —S(CH$_2$)$_2$—, —(CH$_2$)$_2$S—, —CH$_2$SO$_2$ (CH$_2$)$_2$—, and the like.

"Heteroaryl" means a monovalent monocyclic or bicyclic aromatic radical of 5 to 10 ring atoms containing one or more, preferably one, two, or three ring heteroatoms selected from N, O, or S, the remaining ring atoms being carbon. More specifically the term heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isooxazolyl, benzoxazolyl, benzothiophenyl, benzthiazolyl, quinolinyl, isoquinolinyl, benzopyranyl, and thiazolyl. The heteroaryl ring is optionally substituted with one, two, or three substituents independently selected from alkyl, alkoxy, alkylsulfonyl, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted heteroaryl, cycloalkyloxy, cycloalkenyloxy, optionally substituted phenylcarbonylamino, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)n-R$^a$ (where n is 0 to 2 and R$^a$ is alkyl, haloalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, optionally substituted heteroaralkyl, or optionally substituted heterocycloalkyl), or -alkylene-NHCO—R$^c$ (where R$^c$ is alkyl, haloalkyl, optionally substituted phenyl, optionally substituted phenylalkyl, optionally substituted heteroaryl, optionally substituted heteroaralkyl, or optionally substituted heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro provided heteroaryl is not thieno[2,3-b]pyridine, thieno[3,2-b]pyridine, thieno[3,2-d]pyrimidine, or thieno[2,3-d]pyrimidine. Preferably, methoxy, methyl, ethyl, chloro, trifluoromethyl, fluoro, 2-methoxyethoxy, 2-(morpholin-4-yl)-ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, iso-propoxymethyl, or phenoxymethyl.

When the heteroaryl ring is divalent it has been referred to as heteroarylene in this application.

"Heteroaralkyl" means a -(alkylene)-R radical where R is heteroaryl as defined above.

"Heteroaralkenyl" means a -(alkenylene)-R radical where R is heteroaryl as defined above.

"Keto" means a —C═O group.

"Methylenedioxy" means —O—CH$_2$—O—.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula (I) include compounds wherein a hydroxy, amidino, guanidino, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g, trifluoroacetylamino, acetylamino, and the like), and the like. Prodrugs of compounds of Formula (I) are also within the scope of this invention.

The present invention also includes N-oxide derivatives and protected derivatives of compounds of Formula (I). For example, when compounds of Formula (I) contain an oxidizable nitrogen atom, the nitrogen atom can be converted to an N-oxide by methods well known in the art. Also when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. 1999, the disclosure of which is incorporated herein by reference in its entirety. The protected derivatives of compounds of Formula (I) can be prepared by methods well known in the art.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated.

Certain compounds of Formula (I) can exist as tautomers. All possible tautomers are within the scope of this invention. Additionally, as used herein the terms alkyl, alkylene, alkenylene, and alkynylene includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth.

"Optionally substituted phenyl" means a phenyl ring optionally substituted with one, two, or three substituents independently selected from alkyl, halo, alkoxy, alkylthio, haloalkyl, haloalkoxy, heteroaryl (that is optionally substituted with one or two substituents independently selected from alkyl, halo, hydroxy, alkoxy, carboxy, amino, alkylamino, or dialkylamino), heterocycloalkyl (that is optionally substituted with one or two substituents independently selected from alkyl, halo, hydroxy, alkoxy, carboxy, amino, alkylamino, or dialkylamino), amino, alkylamino, dialkylamino, hydroxy, cyano, nitro, methylenedioxy, aminocarbonyl, hydroxyalkyl, alkoxycarbonyl, aminoalkyl (preferably, -(alkylene)NRR' where R and R' are independently hydrogen or alkyl), or carboxy or optionally substituted with five fluorine atoms. When the phenyl is substituted it is referred herein as "substituted phenyl".

"Optionally substituted phenylcarbonylamino" means a —NHCOR radical where R is optionally substituted phenyl as defined above e.g., benzoylamino, and the like.

"Optionally substituted phenylalkyl" means a -(alkylene)-R radical where R is optionally substituted phenyl as defined above e.g., benzyl, phenylethyl, and the like.

"Optionally substituted phenoxyalkyl or optionally substituted phenyloxyalkyl" means a -(alkylene)-OR radical where R is optionally substituted phenyl as defined above e.g., phenoxymethyl, phenoxyethyl, and the like.

"Optionally substituted heteroaryl" means a monovalent monocyclic or bicyclic aromatic radical of 5 to 10 ring atoms containing one or more, preferably one, two, or three ring heteroatoms selected from N, O, or S, the remaining ring atoms being carbon. The heteroaryl ring is optionally substituted with one, two, or three substituents independently selected from alkyl, halo, alkoxy, haloalkyl (preferably trifluoromethyl), haloalkoxy (preferably trifluoromethoxy), amino, alkylamino, dialkylamino, hydroxy, cyano, nitro, aminocarbonyl, hydroxyalkyl, alkoxycarbonyl, aminoalkyl (preferably, -(alkylene)NRR' where R and R' are independently hydrogen or alkyl), optionally substituted phenyl, optionally substituted phenoxy, carboxy, or heteroaryl that is optionally substituted with alkyl, halo, hydroxy, alkoxy, carboxy, amino, alkylamino, or dialkylamino. More specifically the term optionally substituted heteroaryl includes, but is not limited to, pyridyl, pyrrolyl, imidazolyl, thienyl, furanyl, indolyl, quinolyl, pyrazine, pyrimidine, pyridazine, oxazole, isooxazolyl, benzoxazole, quinoline, isoquinoline, benzopyranyl, and thiazolyl. When the heteroaryl is substituted it is referred herein as "substituted heteroaryl".

"Optionally substituted heteroaryloxy" means a —OR radical where R is optionally substituted heteroaryl ring as defined above.

"Optionally substituted heteroaralkyloxy" means a —OR radical where R is optionally substituted heteroaralkyl ring as defined below.

"Optionally substituted heteroaryloxyalkyl" means a -(alkylene)-OR radical where R is optionally substituted heteroaryl ring as defined above.

"Optionally substituted heteroaralkyl" means a -(alkylene)-R radical where R is optionally substituted heteroaryl ring as defined above.

"Optionally substituted heterocycloalkyl" means a heterocycloalkyl group as defined above which is optionally substituted with one, two, or three substituents independently selected from alkyl, cycloalkyl, cycloalkylalkyl, halo, alkoxy, haloalkyl, haloalkoxy, amino, alkylamino, dialkylamino, hydroxy, cyano, nitro, optionally substituted phenylalkyl, optionally substituted heteroaralkyl, aminocarbonyl, hydroxyalkyl, alkoxycarbonyl, aminoalkyl, or carboxy. Preferably, optionally substituted with one, two, or three substituents independently selected from alkyl, halo, alkoxy, haloalkyl, haloalkoxy, amino, alkylamino, dialkylamino, hydroxy, cyano, nitro, optionally substituted phenylalkyl, optionally substituted heteroaralkyl, aminocarbonyl, hydroxyalkyl, alkoxycarbonyl, aminoalkyl (preferably, -(alkylene)NRR' where R and R' are independently hydrogen or alkyl), or carboxy. When the heterocycloalkyl is substituted it is referred herein as "substituted heterocycloalkyl".

"Optionally substituted heterocycloalkyloxy" means a —OR radical where R is optionally substituted heterocycloalkyl ring as defined above.

"Optionally substituted heterocycloalkylalkyl" means a -(alkylene)-R radical where R is optionally substituted heterocycloalkyl ring as defined above.

"Optionally substituted heterocycloalkylalkyloxy" means a —OR radical where R is optionally substituted heterocycloalkylalkyl ring as defined above.

"Optionally substituted heterocycloalkyloxyalkyl" means a -(alkylene)-OR radical where R is optionally substituted heterocycloalkyl as defined above e.g., piperidinyloxymethyl, pyrrolidinyloxyethyl, and the like.

"Optional" or "optionally" means that the subsequently described event or circumstance may but need not occur, and that the description includes instances where the event or circumstance occurs and instances in which it does not. For example, "heterocycloalkyl group optionally mono- or di-substituted with an alkyl group" means that the alkyl may but need not be present, and the description includes situations where the heterocycloalkyl group is mono- or disubstituted with an alkyl group and situations where the heterocycloalkyl group is not substituted with the alkyl group.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Substituted heteroalkyl" means heteroalkyl as defined above that is substituted with one or two groups independently selected from hydroxy, amino, alkylamino, or dialkylamino.

"Treating" or "treatment" of a disease includes:

preventing the disease, i.e. causing the clinical symptoms of the disease not to develop in a mammal that may be exposed to or predisposed to the disease but does not yet experience or display symptoms of the disease;

inhibiting the disease, i.e., arresting or reducing the development of the disease or its clinical symptoms; or relieving the disease, i.e., causing regression of the disease or its clinical symptoms.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

PREFERRED EMBODIMENTS

While the broadest definition of this invention is set forth in the Summary of the Invention, certain compounds of Formula (I) are preferred. For example:

1. A preferred group of compounds is that wherein Z is —CONR$^3$—, —NR$^4$CO—, —SO$_2$NR$^5$—, —NRSO$_2$—, —NR$^7$CONR$^8$—, or —NR$^9$SO$_2$NR$^{10}$— where R$^3$–R$^{10}$ are independently selected from hydrogen, alkyl, hydroxyalkyl, alkoxyalkyl, aralkyl, or heteroaralkyl, preferably R$^3$-R$^{10}$ are hydrogen. More preferably, Z is —CONH—, —SO$_2$NH—, or —NHCONH—. Most preferably, Z is —CONH—.

(a) Within the above preferred group (1) and the more preferred groups contained therein, an even more preferred group of compounds is that wherein:

R is hydrogen;

Ar$^1$ is arylene optionally substituted with one or two substituents independently selected from alkyl, halo, or haloalkyl, preferably Ar$^1$ is phenylene with one or two substituents independently selected from methyl, fluoro or trifluoromethyl. More preferably, Ar$^1$ is phenylene and the triple bond attached to Ar$^1$ is in the para position relative to the —CONHOH group.

(b) Within the above preferred (1) and the more preferred groups contained therein, another even more preferred group of compounds is that wherein:

R is hydrogen;

Ar$^1$ is heteroarylene optionally substituted with one or two substituents independently selected from alkyl, halo, or haloalkyl. Preferably, Ar$^1$ is thiophenyl.

(i) Within the above preferred, more preferred group, and even more preferred groups i.e., (1), (a) and (b) and the preferred groups contained therein, a particularly preferred group of compounds is that wherein:

X and Y are bond; and

R$^1$ and R$^2$ are independently hydrogen or alkyl, preferably hydrogen or methyl, more preferably hydrogen.

(ii) Within the above preferred, more preferred group, and an even more preferred groups i.e., (1), (a) and (b) and the preferred groups contained therein, another particularly preferred group of compounds is that wherein:

X and Y are independently bond or alkylene provided that both are not bond, preferably bond, methylene, ethylene, or propylene, more preferably bond or methylene; and R$^1$ and R$^2$ are independently hydrogen or alkyl, preferably hydrogen or methyl, more preferably hydrogen.

(iii) Within the above preferred, more preferred group, and an even more preferred groups i.e., (1), (a) and (b) and the preferred groups contained therein, yet another particularly preferred group of compounds is that wherein:

X and Y are bond; and

R$^1$ and R$^2$ together with the carbon atom to which they are attached form cycloalkylene, preferably cyclopropylene, cyclopentylene, cyclohexylene, or cycloheptylene.

(iv) Within the above preferred, more preferred group, and an even more preferred groups i.e., (1), (a) and (b) and the preferred groups contained therein, yet another particularly preferred group of compounds is that wherein:

X and Y are bond; and

R$^1$ and R$^2$ together with the carbon atom to which they are attached form heterocycloalkylene, preferably piperidin-4-yl optionally substituted with alkyl or haloalkyl, preferably methyl, ethyl, or 2,2,2-trifluoroethyl.

(v) Within the above preferred, more preferred group, and an even more preferred groups i.e., (1), (a) and (b) and the preferred groups contained therein, another particularly preferred group of compounds is that wherein:

X and Y are independently bond or alkylene provided that both are not bond, preferably bond, methylene, ethylene, or propylene, more preferably bond or methylene; and R$^1$ and R$^2$ together with the carbon atom to which they are attached form cycloalkylene, preferably cyclopropylene, cyclopentylene, cyclohexylene, or cycloheptylene.

(vi) Within the above preferred, more preferred group, and an even more preferred groups i.e., (1), (a) and (b) and the preferred groups contained therein, another particularly preferred group of compounds is that wherein:

X and Y are independently bond or alkylene provided that both are not bond, preferably bond, methylene, ethylene, or propylene, more preferably bond or methylene; and R$^1$ and R$^2$ together with the carbon atom to which they are attached form heterocycloalkylene, preferably piperidin-4-yl optionally substituted with alkyl or haloalkyl, preferably methyl, ethyl, or 2,2,2-trifluoroethyl.

Within the above preferred, more preferred group, an even more preferred, and particularly preferred groups of compounds i.e., (1), (a), (b) and (i)-(vi) and the preferred groups contained therein, a more particularly preferred group of compounds is that wherein:

Ar$^2$ is aryl. Preferably, Ar$^2$ is phenyl optionally substituted with one, two, or three substituents independently selected from alkyl, alkoxy, alkoxyalkyl, halo, haloalkyl, haloalkoxy, alkylamino, dialkylamino, hydroxy, hydroxyalkyl, hydroxyalkyloxy, aminoalkyl, aminoalkoxy, alkoxyalkyloxy, optionally substituted phenyloxyalkyl, optionally substituted heteroaralkyloxy, optionally substituted heteroaryloxyalkyl, optionally substituted heterocycloalkylalkyloxy, or optionally substituted heterocycloalkylalkyl. Preferably, one, two, or three substituents independently selected from methyl, ethyl, methoxy, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, 2-morpholino-4-ylethyl, morpholino-4-ylmethyl, N,N-dimethylaminomethyl, iso-propoxymethyl, or phenoxymethyl.

Within the above preferred, more preferred group, an even more preferred, and particularly preferred groups of compounds i.e., (1), (a), (b) and (i)-(vi) and the preferred groups contained therein, another more particularly preferred group of compounds is that wherein:

Ar$^2$ is heteroaryl. Preferably, Ar$^2$ is thiophenyl, pyridinyl, quinolinyl, thiazolyl, benzthiazolyl, benzoxazolyl, furanyl, benzimidazolyl, benzothiophenyl, pyrrolyl, indolyl, isoindolyl, or isoquinolinyl optionally substituted with one or two substituents independently selected from alkyl, alkoxy, alkoxyalkyl, halo, haloalkyl, haloalkoxy, alkylamino, dialkylamino, hydroxy, hydroxyalkyl, hydroxyalkyloxy, aminoalkyl, aminoalkoxy, alkoxyalkyloxy, optionally substituted phenyl, optionally substituted heteroaryl, optionally substituted phenyloxyalkyl, optionally substituted heteroaralkyloxy, optionally substituted heteroaryloxyalkyl, optionally substituted heterocycloalkylalkyloxy, or optionally substituted heterocycloalkylalkyl. Preferably, one or two substituents independently selected from methyl, ethyl, methoxy, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, 2-morpholino-4-ylethyl, morpholino-4-ylmethyl, N,N-dimethylamino-methyl, 2-N,N-dimethylaminoethyl, aminomethyl, iso-propoxymethyl, phenyl, or phenoxymethyl. More preferably $Ar^2$ is 4-phenylthiazol-2-yl, 2-(4-$H_2NCH_2$phenyl)oxazol-5-yl, benzothiophen-2-yl, 5-Cl-benzofuran-2-yl, 5-Cl-indol-2-yl, benzofuran-2-yl, indol-2-yl, 3-($CF_3CH_2OCH_2$)benzofuran-2-yl, benzothiazol-2-yl, 4-$CF_3$-benzothiophen-2-yl, benzimidazol-2-yl, 5-F-benzothiophen-2-yl, 3-$(CH_3)_2N(CH_2)_2$-benzofuran-2-yl, 1-$(CH_3)_2N(CH_2)_2$-benzoimidzol-2-yl, 4-$(CH_3)_2N(CH_2)_2O$-quinolin-2-yl, or 4—$CH_3O$-quinolin-2-yl.

2. Yet another preferred group of compound of Formula (I) is represented by Formula (Ia):

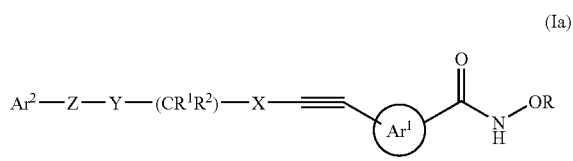

where:

$Ar^2$ is aryl or heteroaryl and other groups are as defined in the Summary of the Invention.

(a) Within the above preferred group (2), an even more preferred group of compounds is that wherein:

R is hydrogen;

Z is —CONH—; and $Ar^1$ is arylene optionally substituted with one or two substituents independently selected from alkyl, halo, or haloalkyl, preferably $Ar^1$ is phenylene with one or two substituents independently selected from methyl, fluoro or trifluoromethyl. More preferably, $Ar^1$ is phenylene and the triple bond attached to $Ar^1$ is in the para position relative to the —CONHOH group.

(b) Within the above preferred group (2), another even more preferred group of compounds is that wherein:

R is hydrogen;

Z is —CONH—; and $Ar^1$ is heteroarylene optionally substituted with one or two substituents independently selected from alkyl, halo, or haloalkyl, more preferably methyl, fluoro, or trifluoromethyl.

(i) Within the above preferred, more preferred group, and an even more preferred groups i.e., (2), (a) and (b) and the preferred groups contained therein, a particularly preferred group of compounds is that wherein:

X and Y are bond; and $R^1$ and $R^2$ are independently hydrogen or alkyl, preferably hydrogen or methyl, more preferably hydrogen.

(ii) Within the above preferred, more preferred group, and an even more preferred groups i.e., (2), (a) and (b) and the preferred groups contained therein, another particularly preferred group of compounds is that wherein:

X and Y are independently bond or alkylene provided that both are not bond, preferably bond, methylene, ethylene, or propylene, more preferably bond or methylene; and $R^1$ and $R^2$ are independently hydrogen or alkyl, preferably hydrogen or methyl, more preferably hydrogen.

(iii) Within the above preferred, more preferred group, and an even more preferred groups i.e., (2), (a) and (b) and the preferred groups contained therein, yet another particularly preferred group of compounds is that wherein:

X and Y are bond; and $R^1$ and $R^2$ together with the carbon atom to which they are attached form cycloalkylene, preferably cyclopropylene, cyclopentylene, cyclohexylene, or cycloheptylene.

(iv) Within the above preferred, more preferred group, and an even more preferred groups i.e., (2), (a) and (b) and the preferred groups contained therein, yet another particularly preferred group of compounds is that wherein:

X and Y are bond; and $R^1$ and $R^2$ together with the carbon atom to which they are attached form heterocycloalkylene.

(v) Within the above preferred, more preferred group, and an even more preferred groups i.e., (1), (a) and (b) and the preferred groups contained therein, another particularly preferred group of compounds is that wherein:

X and Y are independently bond or alkylene provided that both are not bond, preferably bond, methylene, ethylene, or propylene, more preferably bond or methylene; and $R^1$ and $R^2$ together with the carbon atom to which they are attached form cycloalkylene, preferably cyclopropylene, cyclopentylene, cyclohexylene, or cycloheptylene.

(vi) Within the above preferred, more preferred group, and an even more preferred groups i.e., (1), (a) and (b) and the preferred groups contained therein, another particularly preferred group of compounds is that wherein:

X and Y are independently bond or alkylene provided that both are not bond, preferably bond, methylene, ethylene, or propylene, more preferably bond or methylene; and $R^1$ and $R^2$ together with the carbon atom to which they are attached form heterocycloalkylene, preferably piperidin4-yl optionally substituted with alkyl or haloalkyl, preferably methyl, ethyl, or 2,2,2-trifluoroethyl.

(3). Yet another preferred group of compounds of Formula (I) is represented by Formula (Ib):

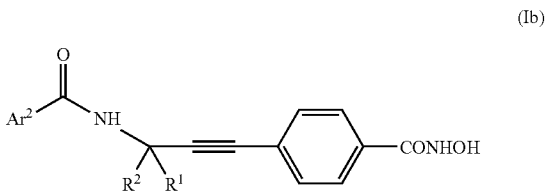

where:

$R^1$ and $R^2$ are independently hydrogen or alkyl, preferably hydrogen or methyl, more preferably hydrogen; and $Ar^2$ is heteroaryl. Preferably, heteroaryl is thiazolyl, quinolinyl, oxazolyl, benzothiophenyl, indolyl, benzofuranyl, benzthiazolyl, or benzimidazolyl optionally substituted with a substitutent selected from halo, haloalkyl, alkoxy, haloalkoxyalkyl, aminoalkoxy, aminoalkyl, alkoxyalkyloxy, alkoxyalkyloxyalkyl, optionally substituted heterocycloalkyloxy, optionally substituted heterocycloalkylalkyloxy, or phenyl optionally substituted with -(alkylene)NRR' where R and R' are independently hydrogen or alkyl, more preferably aminoalkoxy, aminoalkyl, alkoxyalkyloxy, alkoxyalkyloxyalkyl, optionally substituted heterocycloalkyloxy, or optionally substituted heterocycloalkylalkyloxy. More preferably, $Ar^2$ is 4-phenylthiazol-2-yl, 4-MeO-quinolin-2-yl, 2-(4-$H_2NCH_2$phenyl)-oxazol-5-yl, benzothiophen-2-yl, 5-Cl-benzofuran-2-yl, 5-Cl-1H-indol-2-yl, benzofuran-2-yl, 1H-indol-2-yl, 3-($CF_3CH_2OCH_2$)-benzofuran-2-yl, benzthiazol-2-yl, 4-$CF_3$-benzothiophen-2-yl, benzimidazol-2-yl, 5-F-benzothiophen-2-yl, 3-$(CH_3)_2$$NCH_2$-benzofuran-2-yl, 1-$(CH_3)_2N(CH_2)_2$-benzimidzol-2-yl, 4-MeO-benzofuran-2-yl, 4-$(CH_3)_2N(CH_2)_2$O-benzofuran-2-yl, 4-MeO-1H-indol-2-yl, 4-$(CH_3)_2N(CH_2)_2$O-1H-indol-2-yl, 5-MeO-1H-indol-2-yl, 5-$(CH_3)_2N(CH_2)_2$O-1H-indol-2-yl, 3—$CH_3$O $(CH_2)_2OCH_2$-benzofuran-2-yl, 5—$CH_3$O $(CH_2)_2OCH_2$-1H-indol-2-yl, 5-(tetrahydropyran-4-yloxy)-benzofuran-2-yl, 5-(2-pyrrolidin-1-ylethyloxy)benzofuran-2-yl, 5—$CH_3$O $(CH_2)_2$O-benzofuran-2-yl, 5-(1-$CF_3CH_2$-piperidin-4-yloxy)benzofuran-2-yl, 5-(1-cyclopropylpiperidin-4-yloxy)-benzofuran-2-yl, 5-tetrahydropyran-4-ylmethoxy-1H-indol-2-yl, or 5-(2-morpholin-4-ylethoxy)-benzofuran-2-yl.

Reference to the preferred embodiments set forth above is meant to include all combinations of particular and preferred groups.

Representative compounds of Formula (I) are disclosed in Table I-III below.

Compounds of Formula (I) where R and $R^1$ are hydrogen, $Ar^1$ is phenylene, X and Y are bond, Z is —$CONR^3$— where $R^3$ is as defined in Table I below, and $R^2$ and $Ar^2$ are as defined in Table I below are:

TABLE I

| Cpd # | $Ar^2$— | $R^2$ | $R^3$ | |
|---|---|---|---|---|
| 1 | trans phenyl-CH=CH | H | H | |
| 2 | 4-phenylthiazol-2-yl | H | H | |
| 3 | trans phenyl-CH=CH | (S)-$CH_3$ | H | |
| 4 | 4-MeO-quinolin-2-yl | H | H | |
| 5 | 2-(4-$H_2NCH_2$-phenyl)-oxazol-5-yl | H | H | HCl |
| 6 | 4-phenylthiazol-2-yl | (S)-$CH_3$ | H | |
| 7 | phenyl | H | H | |
| 8 | trans phenyl-CH=CH | H | $CH_3$ | |
| 9 | 4-phenylthiazol-2-yl | H | $CH_3$ | |
| 10 | benzothiophen-2-yl | H | H | |
| 11 | 5-Cl-benzofuran-2-yl | H | H | |
| 12 | 5-Cl-1H-indol-2-yl | H | H | |
| 13 | beenzofuran-2-yl | H | H | |
| 14 | benzothiophen-2-yl | (S)-$CH_3$ | H | |
| 15 | 1H-indol-2-yl | H | H | |
| 16 | 3-($CF_3CH_2OCH_2$)-benzofuran-2-yl | H | H | |
| 17 | benzthiazol-22-yl | H | H | |
| 18 | 4-$CF_3$-benzothiophen-2-yl | H | H | |
| 19 | benzimidazol-2-yl | H | H | |
| 20 | benzothiophen-2-yl | H | $CH_3$ | |
| 21 | 5-F-benzothiophen-2-yl | H | H | |
| 22 | 3-$(CH_3)_2NCH_2$-benzofuran-2-yl | H | H | HCl |
| 23 | 1-$(CH_3)_2N(CH_2)_2$-benzimidazol-2-yl | H | H | |
| 24 | 4-MeO-benzofuran-2-yl | H | H | |
| 25 | 4-$(CH_3)_2N(CH_2)_2$O-benzofuran-2-yl | H | H | HCl |
| 26 | 4-MeO-1H-indol-2-yl | H | H | |
| 27 | 4-$(CH_3)_2N(CH_2)_2$O-1H-indol-2-yl | H | H | |
| 28 | 5-MeO-1H-indol-2-yl | H | H | |
| 29 | 5-$(CH_3)_2N(CH_2)_2$O-1H-indol-2-yl | H | H | HCl |
| 30 | 3-$CH_3O(CH_2)_2OCH_2$-beenzofuran-2-yl | H | H | |
| 31 | 5-$CH_3O(CH_2)_2$O-1H-indol-2-yl | H | H | |
| 32 | 5-(tetrahydropyran-4-yloxy)-benzofuran-2-yl | H | H | |
| 33 | 5-(2-pyrrolidin-1-ylethyloxy)benzofuran-2-yl | H | H | HCl |
| 34 | 5-$CH_3O(CH_2)_2$O-benzofuran-2-yl | H | H | |
| 35 | 4-$(CH_3)_2N(CH_2)_2$O-quinolin-2-yl | H | H | HCl |
| 36 | 5-(1-$CF_3CH_2$-piperidin-4-yloxy)benzofuran-2-yl | H | H | |
| 37 | 5-(1-cyclopropylpiperidin-4-yloxy)-benzofuran-2-yl | H | H | HCl |
| 38 | 5-tetrahydropyran-4-ylmethoxy-1H-indol-2-yl | H | H | |
| 39 | 5-(2-morpholin-4-ylethoxy)-benzofuran-2-yl | H | H | HCl | and are named as:

N-hydroxy-4-[3-(3-phenylacryloylamino)prop-1-ynyl]-benzamide;

N-hydroxy-4-[3-(4-phenylthiazol-2-ylcarbonylamino) prop-1-ynyl]-benzamide;

N-hydroxy-4-[3S-(3-phenylacryloylamino)-but-1-ynyl]-benzamide;

N-hydroxy-4-[3-(4-methoxyquinolin-2-ylcarbonylamino) prop-1-ynyl]-benzamide;

N-hydroxy-4-{3-[2-(4-aminomethylphenyl)oxazol-5-yl-carbonylamino)prop-1-ynyl]-benzamide hydrochloride;

N-hydroxy-4-[3S-(4-phenylthiazol-2-ylcarbonylamino) but-1-ynyl]-benzamide;

N-hydroxy-4-[3-(phenylcarbonylamino)prop-1-ynyl]-benzamide;

N-hydroxy-4-{3-[methyl-(3-phenylacryloyl)amino]prop-1-ynyl}benzamide;

N-hydroxy-4-{3-[methyl-(4-phenylthiazol-2-ylcarbonyl) amino]prop-1-ynyl}-benzamide;

N-hydroxy-4-[3-(benzothiophen-2-ylcarbonylamino) prop-1-ynyl]-benzamide;

N-hydroxy-4-[3-(5-chlorobenzofuran-2-ylcarbonylamino)prop-1-ynyl]-benzamide;

N-hydroxy-4-[3-(5-indol-2-ylcarbonylamino)prop-1-ynyl]-benzamide;

N-hydroxy-4-[3-(benzofuran-2-ylcarbonylamino)prop-1-ynyl]-benzamide;

N-hydroxy-4-[3S-(benzothiophen-2-ylcarbonylamino) but-1-ynyl]-benzamide;

N-hydroxy-4-[3-(indol-2-ylcarbonylamino)prop-1-ynyl]-benzamide;

N-hydroxy-4-{3-[3-(2,2,2-trifluoroethyloxymethyl)benzofuran-2-yl-carbonyl-amino]prop-1-ynyl}-benzamide;

N-hydroxy-4-[3-(benzthiazol-2-ylcarbonylamino)prop-1-ynyl]-benzamide;

N-hydroxy-4-[3-(4-trifluoromethylbenzothiophen-2-yl-carbonyl-amino)prop-1-ynyl]-benzamide;

N-hydroxy-4-[3-(benzimidazol-2-ylcarbonylamino)prop-1-ynyl]-benzamide;

N-hydroxy-4-{3-[methyl-(benzothiophen-2-ylcarbonyl) amino]prop-1-ynyl}-benzamide;

N-hydroxy-4-[3-(5-fluorobenzothiophen-2-ylcarbonylaminoprop-1-ynyl]-benzamide;

N-hydroxy-4-[3-(3-N,N-dimethylaminomethylbenofuran-2-ylcarbonylamino)prop-1-ynyl]-benzamide hydrochloride;

N-hydroxy-4-{3-[1-(2-N,N-dimethylaminoethyl)benzimidazol-2-ylcarbonyl-amino]prop-1-ynyl}benzamide;

N-hydroxy-4-[3-(4-methoxybenzofuran-2-ylcarbonylamino)prop-1-ynyl]-benzamide;

N-hydroxy-4-[3-(4-N,N-dimethylaminoethoxybenzofuran-2-ylcarbonylamino)prop-1-ynyl]-benzamide hydrochloride;

N-hydroxy-4-[3-(4-methoxyindol-2-ylcarbonylamino) prop-1-ynyl]-benzamide;

N-hydroxy-4-[3-(4-N,N-dimethylaminoethoxyindol-2-yl-carbonylamino)prop-1-ynyl]-benzamide;

N-hydroxy-4-[3-(5-methoxyindol-2-ylcarbonylamino) prop-1-ynyl]-benzamide;

N-hydroxy-4-[3-(5-N,N-dimethylaminoethoxyindol-2-ylcarbonyl-amino)prop-1-ynyl]-benzamide hydrochloride;

N-hydroxy-4-{3-[3-(2-methoxyethyloxymethyl)benzofuran-2-yl-carbonylamino]prop-1-ynyl}benzamide;

N-hydroxy-4-{3-[3-(2-methoxyethyloxy)indol-2-yl-carbonylamino]prop-1-ynyl}-benzamide;

N-hydroxy-4-[3-(5-tetrahydropyran-4-yloxybenzofuran-2-yl-carbonylamino)prop-1-ynyl]benzamide;

N-hydroxy-4-{3-[5-(2-pyrrolidin-1-ylethoxy)benzofuran-2-yl-carbonylamino]prop-1-ynyl}benzamide hydrochloride;

N-hydroxy-{3-[5-(2-methoxyethyloxy)benzofuran-2-yl-carbonylamino]prop-1-ynyl}-benzamide;

N-hydroxy-4-{3-[4-(N,N-dimethylaminoethyloxy)quinolin-2-yl-carbonylamino]prop-1-ynyl}benzamide hydrochloride;

N-hydroxy-4-{3-[5-(1-(2,2,2-trifluoroethyl)piperidin-4-yloxy)benzofuran-2-ylcarbonyl-amino]prop-1-ynyl}benzamide;

N-hydroxy-4-{3-[5-(1-cyclopropylpiperidin-4-yloxy) benzofuran-2-yl-carbonylamino]-prop-1-ynyl}benzamide hydrochloride;

N-hydroxy-4-{3-[5-(tetrahydropyran-4-ylmethyloxy) benzofuran-2-ylcarbonylamino]-prop-1-ynyl}benzamide; and N-hydroxy-4-{3-[5-(2-morpholin-4-ylethyloxy)benzofuran-2-yl-carbonylamino]prop-1-ynyl}benzamide hydrochloride.

Compounds of Formula (I) where $Ar^1$ is phenylene, X and Y are bond, R, $R^1$ and $R^2$ are hydrogen, Z and $Ar^2$ are as defined in Table II below are:

TABLE II

| Cpd. # | $Ar^2$— | Z |
|---|---|---|
| 1 | 4-Cl-phenyl | —NHCONH— |
| 2 | 4-$CF_3$-phenyl | —NHCONH— |
| 3 | phenyl | —NHCONH— |
| 4 | 2-$CF_3$O-phenyl | —NHCONH— |
| 5 | phenyl | —$SO_2$NH— | and are named as:

N-hydroxy-4-{3-[3-(4-chlorophenyl)ureido]prop-1-ynyl}benzamide;

N-hydroxy-4-{3-[3-(4-trifluoromethylphenyl)ureido] prop-1-ynyl}benzamide;

N-hydroxy-4-{3-[3-(phenyl)ureido]prop-1-ynyl}benzamide;

N-hydroxy-4-{3-[3-(2-trifluoromethoxyphenyl)ureido] prop-1-ynyl}benzamide; and

N-hydroxy-4-[3-(phenylsulfonylamino)prop-1-ynyl]-benzamide.

Compounds of Formula (1) where $Ar^1$ is phenylene, X and Y are bond, R is hydrogen, Z is —CONH—, $R^1$, $R^2$, and $Ar^2$ are as defined in Table III below are:

TABLE III

| Cpd # | $Ar^2$— | >$CR^1R^2$ |
|---|---|---|
| 1 | trans phenyl-CH=CH | >$C(CH_3)_2$ |
| 2 | 4-phenylthiazol-2-yl | >$C(CH_3)_2$ |
| 3 | benzothiophen-2-yl | >$C(CH_3)_2$ |
| 4 | benzofuran-2-yl | >$C(CH_3)_2$ |
| 5 | benzofuran-2-yl | cyploroylene |
| 6 | 1H-indol-2-yl | cyproylene |
| 7 | benzofuran-2-yl | cyclobutylene |
| 8 | benzofuran-2-yl | cyclopentylene |
| 9 | benzofuran-2-yl | cyclohexylene |
| 10 | 1H-indol-2-yl | cyclohexylene |
| 11 | benzofuran-2-yl | cycloheptylene |
| 12 | 1H-indol-2-yl | cycloheptylene |
| 13 | 1H-indol-2-yl | cyclopentylene |
| 14 | 1H-indol-2-yl | cyclobutylene |
| 15 | benzothiophen-2-yl | cyclopropylene |

TABLE III-continued

| Cpd # | Ar²— | >CR¹R² | |
|---|---|---|---|
| 16 | 1H-indol-2-yl | tetrahydropyran-4-yl | |
| 17 | 4-CH₃O-1H-indol-2-yl | cyclopropylene | |
| 18 | 5-CH₃O-1H-indol-2-yl | cyclopropylene | |
| 19 | 1H-indol-2-yl | piperidin-4-yl | |
| 20 | benzofuran-2-yl | piperidin-4-yl | HCl |
| 21 | 1H-indol-2-yl | 1-CF₃CH₂piperidin-4-yl | | and are named as:

N-hydroxy-4-[3-methyl-3-(3-phenylacryloylamino)but-1-ynyl]-benzamide;

N-hydroxy-4-[3-methyl-3-(4-phenylthiazol-2-ylcarbonylamino)but-1-ynyl]-benzamide;

N-hydroxy-4-[3-methyl-3-(benzthiazol-2-ylcarbonylamino)but-1-ynyl]-benzamide;

N-hydroxy-4-[3-methyl-3-(benzofuran-2-ylcarbonylamino)but-1-ynyl]-benzamide,

N-hydroxy-4-[1-(benzofuran-2-yl-carbonylamino)-cycloprop-1-ylethynyl]-benzamide;

N-hydroxy-4-[1-(1H-indol-2-yl-carbonylamino)-cycloprop-1-yl-ethynyl]-benzamide;

N-hydroxy-4-[1-(benzofuran-2-ylcarbonylamino)-cyclobut-1-yl-ethynyl]-benzamide;

N-hydroxy-4-[1-(benzofuran-2-ylcarbonylamino)-cyclohept-1-yl-ethynyl]-benzamide;

N-hydroxy-4-[1-(benzofuran-2-ylcarbonylamino)-cyclohex-1-yl-ethynyl]-benzamide;

N-hydroxy-4-[1-(1H-indol-2-yl-carbonylamino)-cyclohex-1-yl-ethynyl]-benzamide;

N-hydroxy-4-[1-(benzofuran-2-ylcarbonylamino)-cyclohept-1-yl-ethynyl]-benzamide;

N-hydroxy-4-[1-(1H-indol-2-yl-carbonylamino)-cyclohept-1-yl-ethynyl]-benzamide;

N-hydroxy-4-[1-(1H-indol-2-yl-carbonylamino)-cyclopent-1-yl-ethynyl]-benzamide;

N-hydroxy-4-[1-(1H-indol-2-yl-carbonylamino)-cyclobut-1-yl-ethynyl]-benzamide;

N-hydroxy-4-[1-(benzothiophen-2-yl-carbonylamino)-cycloprop-1-yl-ethynyl]-benzamide;

N-hydroxy-4-[4-(1H-indol-2-yl-carbonylamino)tetrahydrofuran-4-yl-ethynyl]-benzamide;

N-hydroxy-4-[1-(4-methoxyindol-2-yl-carbonylamino)-cycloprop-1-yl-ethynyl]-benzamide;

N-hydroxy-4-[1-(5-methoxyindol-2-yl-carbonylamino)-cycloprop-1-yl-ethynyl]-benzamide;

N-hydroxy-4-[4-(1H-indol-2-yl-carbonylamino)piperidin-4-yl-ethynyl]-benzamide;

N-hydroxy-4-[4-(benzofuran-2-yl-carbonylamino)piperidin-4-yi-ethynyl]-benzamide hydrochloride; and N-hydroxy-4-[4-(1H-indol-2-yl-carbonylamino)-1-(2,2,2-trifluoroethyl)piperidin-4-yl-ethynyl]-benzamide.

General Synthesis

Compounds of this invention can be made by the methods depicted in the reaction scheme shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (1) where Z is —CONR³—, —SO₂NR⁵—, —NR⁷CONR⁸—, —NR⁹SO₂NR¹⁰—, or —OCONR¹¹— and other groups are as defined in the Summary of the Invention can be prepared by the procedure illustrated and described in Scheme A below.

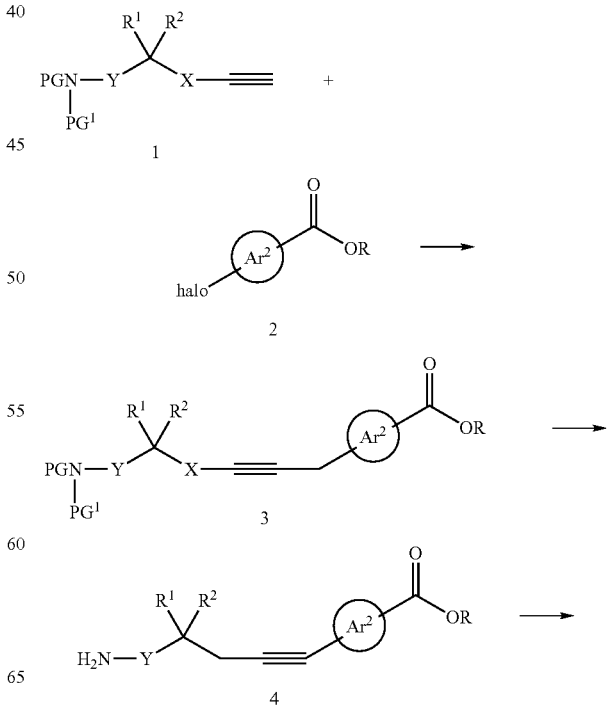

-continued

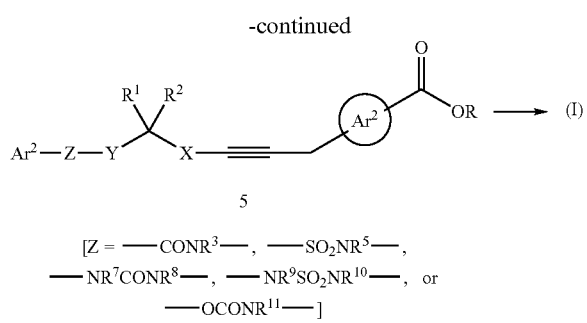

[Z = —CONR³—, —SO₂NR⁵—,
—NR⁷CONR⁸—, —NR⁹SO₂NR¹⁰—, or
—OCONR¹¹—]

Reaction of an alkyne of formula 1 (where PG is a suitable amino protecting group and $PG^1$ is hydrogen or a suitable amino protecting group such as tert-butoxycarbonyl, benzyloxycarbonyl, and the like, more preferably tert-butoxycarbonyl), with a compound of formula 2 (where R is alkyl, preferably methyl or ethyl and the halo group is preferably iodo), provides a compound of formula 3. The reaction is carried out in a suitable organic solvent such as dimethylformamide and in the presence of an organic base such as triethylamine, and the like and a suitable catalyst such as $PdCl_2(Ph_3P)_2$, and the like.

Compounds of formula I can be prepared from commercially available starting materials by methods well known in the art. For example, N-tert-butoxycarbonyl-propargylamine can be prepared by reacting commercially available propargylamine with tert-butoxycarbonyl anhydride in the presence of a base such as triethylamine, ethylisopropylamine, and the like. Compounds of formula I can also be prepared from N-protected amino acids by first reducing the acid group to give the corresponding aldehyde by methods well known in the art and then reacting the aldehyde with Ohira reagent (see Ohira, S. *Synth. Commun.*, 19, 561-564, (1989)) to give a compound of formula 1. A detailed synthesis of a compound of formula 1 where X and Y are bond, $R^1$ and $R^2$ are methyl, and PG is tert-butoxycarbonyl and $PG^1$ is hydrogen from 2-aminoisobutyric acid by the above method is provided in working Example 3 below. Amino acids suitable for preparing compounds of formula 1 are commercially available. For example, 1-amino-cyclobutanecarboxylic acid, homoalanine, aspartic acid, gamma-n-butyric acid, 3-amino-3-phenylpropionic acid, 4-amino-2,2-dimethyl butyric acid, piperidine-3-carboxylic acid, 4-aminopiperidine-4-carboxylic acid, 4-amino-4-carboxytetrahydropyran, 2-aminocyclopentaneacetic acid, and 2-amino-1-cyclopentanecarboxylic acid are commercially available. Alpha and beta amino acids can also be prepared by methods described in Duthaler, R. O. *Tetrahedron*, 50, 1539-1650 (1994) and Cole, D. C. *Tetrahedron*, 50, 9517-9582, (1994), the disclosures of which are incorporated herein by reference in their entirety.

Compounds of formula 1 where $PG^1$ is an amino protecting group can also be prepared from commercially available alcohols under Mitsunobu reaction conditions. A detailed description of the synthesis of a compound of formula 1 by this procedure is provided in working Example 2 below.

Removal of the amino-protecing group provides a compound of formula 4. The reaction conditions employed depend on the nature of the protecting group. For example, if the amino-protecting group is tert-butoxycarbonyl, it is removed by treating a compound of formula 3 with an acid such as trifluoroacetic acid, hydrochloric acid, and the like, in a suitable organic solvent such as dioxane, tetrahydrofuran, methanol, dichloromethane, and the like.

Compounds of formula 2 are either commercially available or they can be prepared by methods well known in the art. For example, methyl 4-iodobenzoate is commercially available. 4-Iodo-2-thiophenecarboxylic methyl ester can be prepared from commercially available 4-iodo-2-thiophenecarboxylic acid under standard esterification reaction conditions.

Compound 4 is then then converted to a compound of formula 5 where Z is —CONR³—, —SO₂NR⁵—, —NR⁷CONR⁸—, —NR⁹SO₂NR¹⁰—, or —OCONR¹¹— by methods well known in the art. Some such methods are described below.

A compound of formula 5 where Z is —CONH— or —SO₂NH— is prepared by reacting a compound of formula 4 with an acylating or sulfoylating agent of formula Ar²COL or Ar²SO₂L respectively, where L is a leaving group under acylating or sulfonylating reaction conditions such as halo (particularly chloro or bromo). Suitable for solvents for the reaction include organic solvents such as dichloromethane, tetrahydrofuran, dioxane, dimethylformamide, and the like. The reaction is carried out in the presence of an organic base such as triethyamine, pyridine, and the like. Acylating or sulfonylating agent of formula Ar²COL or Ar²SO₂L are either commercially available or they can be readily prepared by methods well known in the art. For example, Ar²COL can be prepared by reacting the corresponding acids with a halogenating agent such as oxalyl chloride, thionyl chloride, and the like.

Alternatively, a compound of Formula (I) when Z is —CONH— can be prepared by heating 4 with an acid anhydride. Suitable solvents for the reaction are tetrahydrofuran, dioxane, and the like.

Alternatively, a compound of Formula (I) when Z is —CONH— can be prepared by reacting an acid of formula Ar²—COOH in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC•HCl), or 1,3-dicyclohexylcarbodiimide (DCC), optionally in the presence of 1-hydroxybenzotriazole hydrate (HOBt•H₂O), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, dimethylformamide, ethereal solvents such as tetrahydrofuran, dioxane, and the like. Acids of formula Ar²—COOH such as benzoic acid, cinnamic acid, phenylacetic acid, nicotinic acid, isonicotinic acid, and benzofuran-2-carboxylic acid are commercially available. Others such as 3-phenoxymethylbenzofuran-2-carboxylic acid can be readily prepared from commercially available 3-methylbenzofuran-2-carboxylic acid by first converting it to 2-bromomethylbenzofuran-2-carboxylic acid (brominating it with N-bromosuccinimide under conditions well known in the art) followed by reacting with phenol.

A compound of formula 5 where Z is —NR⁷CONH— is prepared by reacting a compound of formula 4 with an activating agent such as carbonyl diimidazole, followed by displacement of the imidazole group with a primary or secondary amine of formula Ar²NHR⁷. Suitable reaction solvents include tetrahydrofuran, dioxane, and the like.

Alternatively, a compound of formula 5 where Z is —NR⁷CONH— is prepared by reacting compound 4 with a carbamoyl halide of formula Ar²NR⁷COL or an isocyanate of formula Ar²N=C=O under conditions well known in the art.

A compound of formula 5 where Z is —NR⁹SO₂NH— is prepared by reacting a compound of formula 4 with a sulfamoyl halide of formula Ar²NR⁹SO₂L under reaction conditions described in method (a) above. Sulfamoyl halides are either commercially available or may be prepared by methods such as thos described in Graf, R., German Patent 931225 and Catt, J. D. and Matler, W. L., *J. Org. Chem.*, 1974, 39, 577-568.

A compound of formula 5 where Z is —OC(O)NH— is prepared by reacting a compound of formula 4 with acylating agent of formula Ar²OC(O)L under reaction conditions described above.

Compound 5 is then converted to a compound of Formula (I) by reacting it with aqueous hydroxylamine in the presence of a base such as sodium hydroxide and a mixture of organic solvents such as tetrahydrofuran and methanol.

A compound of Formula (I) can be converted to other compounds of Formula (I). For example, a compound of Formula (I) where any of $R^3$-$R^{11}$ is alkyl can also be prepared by reacting a corresponding compound of Formula (I) where any of $R^3$-$R^{11}$ is hydrogen with an alkylating agent under conditions well known in the art. Other methods of preparing compounds of Formula (I) from compound 5 are analogous to the methods disclosed in U.S. Pat. No. 5,998,412 the disclosure of which is incorporated herein by reference in its entirety.

Compounds of Formula (I) where Z is —NR¹²COO— can be prepared by following the procedures described above, by using starting materials such as 3-butyn-2-ol, 3-butyn-1-ol and 4-pentyn-2-ol.

Utility

The compounds of this invention are inhibitors of histone deacetylase enzymes and are therefore useful in the treatment of proliferative diseases such as cancer such as lung, colon, skin, breast, ovarian, prostate, liver, brain and skin, psoriasis, fibroproliferative disorder such as liver fibrosis, smooth muscle proliferative disorder such as atherosclerosis and restenosis, inflammatory diseases such as arthritis, diseases involving angiogenesis such as cancer, diabetic retinopathy, haematopoietic disorder such as anaemia, fungal, parasitic and bacterial infections, viral infection, autoimmune diseases such as arthritis, multiple sclerosis, lupus, allergies, asthma, allergic rhinitis, and organ transplant, and bipolar disorders.

Testing

The ability of the compounds of this invention to inhibit histone deacetylase enzymes can be tested in vitro and in vivo assays described in biological assays Example I and 2 below.

Administration and Pharmaceutical Compositions

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.1-50 mg per kilogram body weight of the recipient per day; preferably about 0.5-20 mg/kg/day. Thus, for administration to a 70 kg person, the dosage range would most preferably be about 35 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral or parenteral using a convenient daily dosage regimen, which can be adjusted according to the degree of affliction. Oral compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art.

Typically, the formulation will contain, on a weight percent (wt %) basis, from about 0.01-99.99 wt % of a compound of Formula (I) based on the total formulation, with the balance being one or more suitable pharmaceutical excipients. Preferably, the compound is present at a level of about 1-80 wt %. Representative pharmaceutical formulations containing a compound of Formula (I) are described below.

As stated previously, the compounds of this invention can be administered in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The compounda of the present invention are particularly useful when adminsitered in combination with radiation therapy. Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGFR.

Preferred estrogen receptor modulators are tamoxifen and raloxifene.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds that interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds that interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl) retinamide, and N-4-carboxyphenyl retinamide.

"Cytotoxic agents" refer to compounds which cause cell death primarily by interfering directly with the cell's functioning or inhibit or interfere with cell mitosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro)platinum(II)]-tetrachloride, diarizidinyispermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H, 15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 6,9-bis[(2-aminoethyl)-amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]-adenine, ecteinascidin-743, troxacitabine, 4-[2-amino-4-oxo4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetra cyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabinofuranosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein. It has been reported that (*Int. J. Cancer,* 20, 97(6): 746-50, (2002)) combination therapy with lovastatin, a HMG-CoA reductase inhibitor, and butyrate, an inducer of apoptosis in the Lewis lung carcinoma model in mice showed potentiating antitumor effects Examples of HMG-CoA reductase inhibitors that may be used include but are not limited to lovastatin (MEVACOR®; see U.S. Pat. Nos. 4,231,938, 4,294,926, and 4,319,039), simvastatin (ZOCOR®; see U.S. Pat. Nos. 4,444,784, 4,820, 850, and 4,916,239), pravastatin (PRAVACHOL®; see U.S. Pat. Nos. 4,346,227, 4,537,859, 4,410,629, 5,030,447, and 5,180,589), fluvastatin (LESCOL®; see U.S. Pat. Nos. 5,354,772, 4,911,165, 4,929,437, 5,189,164, 5,118,853, 5,290,946, and 5,356,896), atorvastatin (LIPITOR®; see U.S. Pat. Nos. 5,273,995, 4,681,893, 5,489,691, and 5,342, 952) and cerivastatin (also known as rivastatin and BAY-CHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89, Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and colchicin the use of such salts, esters, open-acid and lactone forms is included within the scope of this invention.

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin.

Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)-1-methyl-2(1H)-quinolinone, (−)-6-[amino(4-chlorophenyl)(1-methyl-1H-imidazol-5-yl) methyl]-4-(3-chloro phenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethy 1]-2-piperazinone, (S)-1-(3-chlorophenyl)-4-[1-(4-cyanobenzyl)-5-imidazolylmethyl]-5-[2-(ethanesulfonyl)-methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxy-methyl-4-(3-chlorobenzyl)-piperidine-1-ylmethyl]-2-methylimidazol-1-ylmethyl}-benzonitrile, 4-{3-[4-(2-oxo-2H-pyridin-1-yl) benzyl]-3H-imidazol-4-ylmethyl}-benzonitrile, 4-{3-[4-(5-chloro-2-oxo-2H-[1,2']bipyridin-5 '-ylmethyl]-3H-imidazol-4-ylmethyl}benzonitrile, 4-{3-[4-(2-oxo-2H-[1,2'] bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6, 10: 12,16-dimetheno-1H-imidazo[4,3-c][1,11,4]dioxa-azacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]-oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacyclo-eicosine-9-carbonitrile, and (+)-19,20-dihydro-3-methyl-19-oxo-5H-18,21-ethano-12, 14-etheno-6,10-metheno-22H-benzo[d]imidazo[4,3-k][1,6, 9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *J. of Cancer*, Vol. 35, No. 9, pp.1394-1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HB Y097, lamivudine, nevirapine, AZT, 3TC, ddC, and ddI. It has been reported ((*Nat. Med.* 8(3):225-32, (2002)) that HIV protease inhibitors, such as indinavir or saquinavir, have potent anti-angiogenic activities and promote regression of Kaposi sarcoma "Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-∝, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib (*PNAS*, Vol. 89, p. 7384 (1992); *JNCI*. Vol. 69, p. 475 (1982); *Arch. Opthalmol*. Vol. 108, p. 573 (1990); *Anat. Rec*. Vol. 238, p. 68 (1994); *FEBS Letters*, Vol. 372, p. 83 (1995); *Clin., Orthop*. Vol. 313, p. 76 (1995); *J. Mol. Endocrinol.*, Vol. 16, p.107 (1996); Jpn. *J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med*. 105:141-145 (1985)), and antibodies to VEGF (see, *Nature Biotechnology*, Vol. 17, pp.963-968 (October 1999); Kim et al., *Nature*, 362, 841-844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 µM or less as measured by the cell or microsomal assay known in the art.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or microsomal assay disclosed hereinunder. Such compounds include, but are not limited to those disclosed in, U.S. Pat. Nos. 5,474,995, 5,861,419, 6,001,843, 6,020,343, 5,409,944, 5,436,265, 5,536,752, 5,550,142, 5,604,260, 5,698,584, 5,710,140, 5,344,991, 5,134,142, 5,380,738, 5,393,790, 5,466,823, 5,633,272, 6,313,138, and 5,932,598, and WO 94/15932, all of which are hereby incorporated by reference. Other examples of specific inhibitors of COX-2 include those disclosed in U.S. Patent the disclosure of which is incorporated herein by reference in its entirety.

General and specific synthetic procedures for the preparation of the COX-2 inhibitor compounds described above are found in U.S. Pat. No. 5,474,995, 5,861,419, and 6,001, 843, all of which are herein incorporated by reference.

Compounds that have been described as specific inhibitors of COX-2 and are therefore useful in the present invention include, but are not limited to, the following:

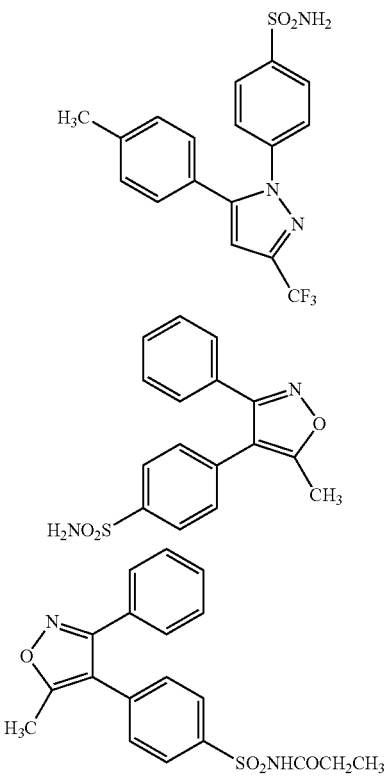

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, U.S. Pat. Nos. 5,344,991, 5,134,142, 5,380,738, 5,393,790, 5,466, 823, 5,633,272, and 5,932,598.

Compounds which are specific inhibitors of COX-2 and are therefore useful in the present invention, and methods of synthesis thereof, can be found in the following patents, pending applications and publications, which are herein incorporated by reference: U.S. Pat. Nos. 5,474,995, 5,861, 419, 6,001,843, 6,020,343, 5,409,944, 5,436,265, 5,536,752, 5,550,142, 5,604,260, 5,698,584, and 5,710,140.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, 5-amino-1-[[3,5-dichloro4-(4-chlorobenzoyl)phenyl]-methyl]-1H-1,2, 3-triazole-4-carboxamide, CM 101, squalamine, combretastatin, RPI4610, NX31838, sulfated mannopentose phosphate, 7,7-(carbonyl-bis[imino-N-methyl-4,2-pyrrolocarbonyl-imino[N-methyl-4,2-pyrrole]-carbonylimino]-bis- (1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_3$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$; $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethyl-phenyl)-5-methylisoxazol-4-carboxamide, 3-[(2,4-dimethylpyrrol-5-yl)methylidenyl)-indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, ST1571, CEP2563, 4-(3-chlorophenylamino)-5,6-dimethyl-7H-pyrrolo [2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, SU 11248, ST157 1A, N-4-chlorophenyl-4-(4-pyridylmethyl)-1-phthalazinamine, and EMD 121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285-292, (1999)). Therefore, the present compounds can serve to inhibit metastasis, alone or in combination with GP IIb/IIIa antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

The term administration and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the farnesyl-protein transferase inhibitors disclosed in U.S. Pat. No. 6,313,138 and an antineoplastic agent. It is also understood that such a combination of antineoplastic agent and inhibitor of farnesyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere® epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloro-methotrexate, mitomycin C, porfiromycin, Herceptin®, Rituxan®, 5-fluorouracil, 6-mercaptopurine, gemcitabine, cytosine arabinoside, podophyllotoxin or podo-phyllotoxin derivatives such as colchicines, etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. The preferred class of antineoplastic agents is the taxanes and the preferred antineoplastic agent is paclitaxel.

Radiation therapy, including x-rays or gamma rays that are delivered from either an externally applied beam or by implantation of tiny radioactive sources, may also be used in combination with the compounds of this invention alone to treat cancer.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Reference A

Synthesis of 3-(2,2,2-trifluoroethoxymethyl)-benzofuran-2-ylcarboxylic acid

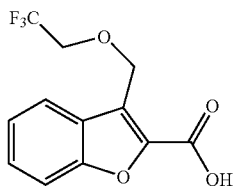

To a suspension of sodium hydride (15 mg, 0.56 mmol) in anhydrous DMF (3 ml) was added 2,2,2-trifluoroethanol (270 μL, 3.7 mmol). The reaction mixture was stirred for 15-20 min and methyl 3-bromomethylbenzofuran-2-carboxylate (prepared as described in Reference C below) was added. Stirring was continued for 8 h, 1N aqueous NaOH was added and the reaction mixture was stirred for additional 10-15 min. The reaction mixture was acidified with 3M aqueous HCl to pH 3 and the product was extracted with ethyl acetate. The organic layer was dried over sodium sulfate and concentrated in vacuo to give crude 3-(2,2,2-trifluoroethoxymethyl)benzofuran-2-carboxylic acid (38 mg, 0.139 mmol), which was used without further purification.

Reference B

Synthesis of 2-[4-(N-Boc-aminomethyl)phenyl]-oxazol-4-ylcarboxylic acid

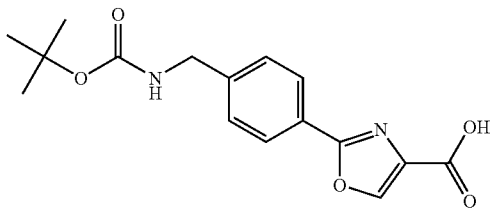

Step 1

To a solution of 4-N-Boc-aminomethylbenzoic acid (25.3 g, 101 mmol) in DMF (50 ml) were added sequentially EDC•HCl (23.9 g, 121 mmol), HOBT (16.3 g, 121 mmol), diisopropylamine (43.8 ml, 252 mmol), and serine methyl ester hydrochloride (18.0 g, 121 mmol). After stirring overnight at room temperature, the reaction was quenched by the addition of water and ethyl acetate. The separated organic layer was washed with 1M aqueous HCl (100 ml), water (100 ml), saturated aqueous sodium bicarbonate solution (100 ml), brine (100 ml), dried over sodium sulfate, and concentrated in vacuo to give methyl 2-[4-(N-Boc-aminomethyl)-benzoylamino]-3-hydroxypropionate (32.0 g, 90.8 mmol) as a white solid.

Step 2

To a solution of methyl 2-[4-(N-Boc-aminomethyl)benzoylamino]-3-hydroxypropionate (32.0 g, 90.8 mmol) in THF (150 ml) was added Burgess' Reagent (26.0 g, 109 mmol) and 3 Å molecular sieves (1 g). The reaction was allowed to stir at 60° C. for 2 h. The reaction mixture was cooled to room temperature and concentrated in vacuo. The crude product was dissolved in dichloromethane and purified by flash chromatography over silica gel with ethyl acetate/dichloromethane (1/1) to give methyl 2-[4-(N-Boc-aminomethyl)-phenyl]-4,5-dihydrooxazol-4-ylcarboxylate (29.5 g, 88.2 mmol) as a pale tan oil.

Step 3

To a solution of methyl 2-[4-(N-Boc-aminomethyl)-phenyl]4,5-dihydrooxazol-4-ylcarboxylate (25.5 g, 76.3 mmol) in dichloromethane (100 ml) was added $CBrCl_3$ (8.23 ml, 83.9 mmol) and DBU (12.5 ml, 83.9 mmol). After stirring at room temperature overnight, the reaction was concentrated and the product isolated by flash chromatography over silica gel. Recrystallization from hot methanol provided methyl 2-[4-(N-Boc-aminomethyl)-phenyl]-oxazole-4-carboxylate (18.4 g, 55.4 mmol) as pale yellow crystals.

Step 4

To a solution of methyl 2-[4-(N-Boc-aminomethyl)-phenyl]-oxazol-4-ylcarboxylate (1.66 g, 5 mmol) in THF (25 ml)/methanol (25 ml) was added 1M aqueous LiOH (25 ml, 25 mmol). After stirring at room temperature for 3 h, the solution was acidified with 2M aqueous HCl to pH 5-6, and partitioned between ethyl acetate (150 ml) and water (150 ml). The organic layer was washed with brine (150 ml), dried over sodium sulfate and concentrated in vacuo giving the title compound as a white solid (1.58 g, 4.96 mmol).

Reference C

Synthesis of methyl 3-(N,N-dimethylaminomethyl)-benzofuran-2-ylcarboxylate

Step 1

To a solution of 3-methyl-benzofuran-2-carboxylic acid (0.98 g, 5.6 mmol) and catalytic amount of DMF (5 drops) in THF (25 ml) was added oxalyl chloride (0.53 ml, 6.1 mmol). After stirring the solution for 1 h at room temperature, methanol (20 ml) and TEA (7.0 ml) were added. The reaction mixture was stirred overnight at room temperature, then concentrated and dissolved in ethyl acetate (100 ml) and washed with aqueous sodium bicarbonate solution (100 ml). The organic layer was dried over sodium sulfate and concentrated to provide crude methyl 3-methylbenzofuran-2-carboxylate (1.0 g, 5.3 mmol) as a tan solid, which was used without further purification.

Step 2

A solution of methyl 3-methylbenzofuran-2-carboxylate (1.0 g, 5.3 mmol), N-bromosuccinimide (0.95 g, 5.3 mmol) and 2,2'-azobisisobutyronitrile (87 mg, 0.53 mmol) was heated to reflux in $CCl_4$ (40 ml) for 3 h, then cooled to room temperature and concentrated. The residue was dissolved in ethyl acetate (100 ml) and washed with water (100 ml). The organic layer was dried over magnesium sulfate and concentrated to provide crude methyl 3-bromomethylbenzofuran-2-carboxylate (1.55 g) as a yellowish solid, which was used in the next step without further purification.

Step 3

To a solution of methyl 3-bromomethylbenzofuran-2-carboxylate (269 mg, 1.0 mmol) in DMF was added dimethylamine (2M solution in THF, 1.5 ml, 3 mmol). The reaction mixture was stirred for 1-2 h, diluted with ethyl acetate (50 ml), washed twice with saturated aqueous sodium bicarbonate solution (50 ml) and finally with brine (50 ml). The organic extract was dried over sodium sulfate and then concentrated in vacuo. Purification by flash chromatography on silica gel (5% methanol in dichloromethane) gave methyl 3-dimethylaminomethylbenzofuran-2-carboxylate (131 mg, 0.57 mmol).

Reference D

Synthesis of 4-methoxy-benzofuran-2-ylcarboxylic acid

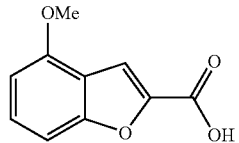

Step 1

To a solution of sodium methoxide (25 wt % solution in methanol, 13.9 ml, 54.5 mmol) in methanol (100 ml) was added a solution of 1,3-cyclohexanedione (7.47 g, 58.0 mmol) in methanol (100 ml). Ethyl bromopyruvate (8.0 ml, 57.4 mmol) dissolved in methanol (50 ml) was added and the resulting mixture was heated at reflux for 2 h, cooled to room temperature and concentrated in vacuo. The residue was dissolved in water (200 ml) and the solution was acidified to pH 1 by addition of 1M aqueous HCl. The resulting mixture was stirred for 5 days at room temperature to yield yellowish white crystals. The crystals were filtered and washed with cold water, dried in vacuo and used without further purification.

Step 2

The crystals obtained above was dissolved in methanol (200 ml) and treated with conc. $H_2SO_4$ (1 ml) and heated at reflux for 2 h. The reaction mixture was cooled to room temperature and concentrated in vacuo. The resulting red oil was diluted in ethyl acetate (150 ml) and washed with saturated sodium bicarbonate solution, brine (100 ml), dried over sodium sulfate, filtered, and concentrated in vacuo. The crude product obtained was purified by flash chromatography over silica gel with ethyl acetate/hexane (1/1) to yield methyl 4-oxo4,5,6,7-tetrahydro-benzofuran-2-ylcarboxylate as a white solid (5.60 g, 28.8 mmol).

Step 3

To a suspension of methyl 4-oxo-4,5,6,7-tetrahydro-benzofuran-2-ylcarboxylate (5.60 g, 28.8 mmol) in $CCl_4$ (200 ml) were added N-bromosuccinimide (5.18 g, 28.8 mmol) and 2,2'-azobisisobutyronitrile (0.483 g, 2.88 mmol). The reaction mixture was heated at reflux for 80 min and concentrated in vacuo. The residue was suspended in ethyl acetate (200 ml), washed with saturated sodium bicarbonate solution (2×50 ml), brine (50 ml), dried over sodium sulfate, filtered, and concentrated in vacuo. The crude product was purified by flash chromatography over silica gel with ethyl acetate/hexane (1/10) to yield methyl 4-hydroxy-benzofuran-2-ylcarboxylate as a while solid (4.21 g, 21.9 mmol).

Step 4

Sodium hydride (32.5 mg, 1.35 mmol) was added to a solution of methyl 4-hydroxy-benzofuran-2-ylcarboxylate (240 mg, 1.25 mmol) in DMF (5 ml). After stirring for 10 min methyl iodide (888 mg, 6.25 mmol) was added and stirring was continued for an additional 1 h. The reaction was carefully quenched with water (30 ml) and diluted with ethyl acetate (50 ml). The separated organic layer was washed with 0.5M aqueous HCl, saturated aqueous sodium bicarbonate solution (50 ml), dried over sodium sulfate, and concentrated in vacuo to give pure methyl 4-methoxy-benzofuran-2-ylcarboxylate (257 mg, 1.25 mmol) as a white solid.

Step 5

To a suspension of methyl 4-methoxy-benzofuran-2-ylcarboxylate (206 mg, 1.0 mmol) in THF/methanol/water (6 ml, 1/1/1) was added 2M aqueous NaOH (1.0 ml) and refluxed until saponification was completed (~3 h). The reaction mixture was acidified with 1M aqueous HCl (10 ml) and diluted with ethyl acetate (30 ml). The separated organic layer was washed with 1M aqueous HCl (30 ml), brine (30 ml), dried over sodium sulfate, and concentrated in vacuo to provide 4-methoxy-benzofuran-2-ylcarboxylic acid as a white solid (189 mg, 0.96 mmol), which was used without further purification.

Reference E

Synthesis of 4-(2-N,N-dimethylamino-ethoxy)-benzofuran-2-ylcarboxylic acid

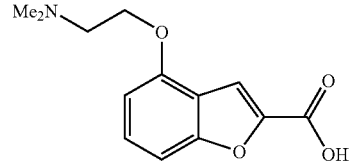

Step 1

To a solution of triphenylphosphine (1.54 g, 5.86 mmol) in anhydrous THF (12 ml) was added DLAD (1.13 ml, 5.86 mmol). The solution was stirred until a white precipitate was formed (2 to 10 min). After additional 60 min a solution of methyl 4-hydroxy-benzofuran-2-ylcarboxylate (750 mg, 3.91 mmol; see Reference D above) and N,N-imethylethanolamine (392 µl, 3.91 mmol) in THF (2 ml) was added and stirring was continued for 16 h. The reaction mixture was concentrated in vacuo and the crude was dissolved in ethyl acetate (20 ml). The product was extracted with 2M aqueous HCl (10 ml). The aqueous layer was washed with ethyl acetate (30 ml), neutralized with saturated sodium bicarbonate solution, and extracted with ethyl acetate. The combined organic extracts were washed with brine, dried over sodium sulfate, and concentrated in vacuo. Flash chromatography over silica gel with ethyl acetate/hexane (9/1) provided methyl 4-(2-N,N-dimethylamino-ethoxy)-benzofuran-2-ylcarboxylate (280 mg, 1.06 mmol) as an highly viscous oil.

Step 2

To a suspension of methyl 4-(2-N,N-dimethylamino-ethoxy)-benzofuran-2-ylcarboxylate (280 mg, 1.06 mmol) in THF/methanol (6 ml, 1/1) was added 2M aqueous NaOH (0.75 ml, 1.5 mmol). The reaction mixture was heated to 70°

C. until saponification was completed (~3 h), cooled to room temperature, and concentrated in vacuo. The residue was acidified with 1M aqueous HCl (2.6 ml) and lyophilized to give crude 4-(2-N,N-dimethylaminoethoxy)-benzofuran-2-ylcarboxylic acid (400 mg) as its hydrochloride salt, which was contaminated with sodium chloride. The crude acid was directly used in the next step without further purification.

Reference F

Synthesis of 4-methoxy-1H-indole-2-carboxylic acid

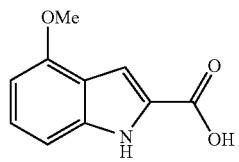

The title compound was synthesized following Step 5 in Reference D starting from commercially available methyl 4-methoxy-1H-indole-2-carboxylate.

Reference G

Synthesis of 4-(2-N,N-dimethylamino-ethoxy)-1H-indole-2-carboxylic acid

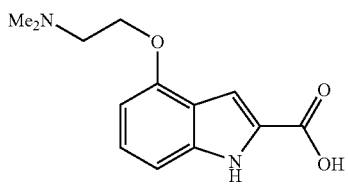

Step 1
Following Step 1 in Reference E starting with 4-hydroxyindole (931 mg, 7.0 mmol) gave 4-(2-N,N-dimethylamino-ethoxy)-1-indole (1.24 g, 6.1 mmol) as a highly viscous oil.
Step 2
To a solution of 4-(2-N,N-dimethylamino-ethoxy)-1-indole (1.24 g, 6.1 mmol) and 4-dimethylaminopyridine (61 mg, 0.61 mmol) in dichloromethane (12 ml) at 0° C. was added di-tert-butyl dicarbonate (1.46 g, 6.69 mmol) followed by triethylamine (1.23 g, 12.2 mmol). The reaction mixture was stirred at 0° C. for 1 h and allowed to warm up to room temperature over 2 h. The mixture was diluted with saturated sodium bicarbonate solution (100 ml) and extracted with dichloromethane. The combined organic layers were dried over sodium sulfate, filtered, and concentrated in vacuo. Purification by flash chromatography over silica gel with ethyl acetate/hexane (4/1) provided 4-(2-N,N-dimethylamino-ethoxy)-1-Boc-indole (577 mg, 1.90 mmol) as highly viscous oil.
Step 3
To a solution of 4-(2-N,N-dimethylamino-ethoxy)-1-Boc-indole (577 mg, 1.90 mmol) in THF (10 ml) at −78° C. was added lithium diisopropylamide (1.8M solution in heptane/THF/ethylbenzene, 1.56 ml, 2.85 mmol). After the reaction mixture was stirred at −78° C. for 1 h gaseous carbon dioxide was introduced over 15 min, and stirring was continued at −78° C. for 1 h. The reaction mixture was allowed to warm up to room temperature over 1 h and quenched with 0.5M aqueous HCl (5 ml). The crude material was concentrated in vacuo and lyophilized to give crude 4-(2-N,N-dimethylamino-ethoxy)-1-Boc-indole-2-carboxylic acid (750 mg) as its hydrochloride salt, which was contaminated with lithium chloride and diisopropylamine hydrochloride salt. The crude acid was directly used in the next step without further purification.
Step 4
To a suspension of crude 4-(2-N,N-dimethylamino-ethoxy)-1-Boc-indole-2-carboxylic acid in dichloromethane (5 ml) was added slowly trifluoroacetic acid (10 ml). The reaction mixture was stirred for 15 min, and concentrated in vacuo to provide crude 4-(2-N,N-dimethylamino-ethoxy)-1H-indole-2-carboxylic acid. The crude acid was purified by HPLC before it was used in the next step.

Reference H

Synthesis of 5-(2-N,N-dimethylamino-ethoxy)-1H-indole-2-carboxylic acid

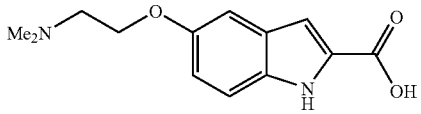

The title compound was synthesized following the procedure in Reference E starting from commercially available ethyl 5-hydroxy-1H-indole-2-carboxylate. The crude acid was purified by HPLC before it was used in the next step.

Reference I

Synthesis of 5-(2-methoxyethoxy)-1H-indole-2-carboxylic acid

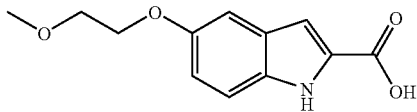

Step 1
A solution of ethyl 5-hydroxy-1H-indole-2-carboxylate (5.0 g, 24.4 mmol) in 1,4-dioxane (50 ml) was treated with triethylamine (6.7 ml, 36.6 mmol) followed by di-tert-butyl dicarbonate (8.0 g, 36.6 mmol) and heated to 70° C. (caution: gas development). After 2 h, the reaction was completed—most of the solvent was removed in vacuo. The residue was dissolved in ethyl acetate (250 ml) and washed with 0.5M aqueous HCl (100 ml), water, and brine. The organic phase was dried over anhydrous sodium sulfate and concentrated in vacuo. The residue was suspended in hexane and the generated precipitate was filtered to provide ethyl N-Boc-5-hydroxy-indole-2-carboxylate (8.2 g, 28.3 mmol) as an off-white solid.
Step 2
To a solution of triphenylphosphine (6.5 g, 24.6 mmol) in anhydrous THF (20 ml) was added DIAD (4.8 ml, 24.6 mmol). The solution was stirred until a white precipitate was formed (2 to 10 min). After additional 60 min, a solution of ethyl N-Boc-5-hydroxy-indole-2-carboxylate (5.0 g, 16.4 mmol) and 1-methoxyethanol (1.3 ml, 16.4 mmol) in THF (20 ml) was added and stirring was continued for 16 h. The reaction mixture was concentrated in vacuo and the residue was suspended in diethyl ether (150 ml). The precipitate was filtered off and the filtrate was concentrated in vacuo. The residue was suspended in hexane and the generated precipitate was filtered off. The filtrated was concentrated in vacuo and purified by flash chromatography over silica gel with ethyl acetate/hexanes (4/1) to provide ethyl N-Boc-5-(2-methoxyethoxy)-indole-2-carboxylate (3.2 g, 8.8 mmol) as a white solid.

Step 3

A solution of ethyl N-Boc-5-(2-methoxyethoxy)-indole-2-carboxylate.(3.2 g, 8.8 mmol) in ethanol (20 ml) was treated with 4M HCl in 1,4-dioxane (20 ml). After 1 h, the solvent was removed in vacuo and the residue was suspended in diethyl ether (50 ml). The generated precipitate was filtered, washed with diethyl ether, and dried in vacuo to provide 5-(2-methoxyethoxy)-1H-indole-2-carboxylate (2.0 g, 7.4 mmol) as an off-white solid.

Step 4

Ethyl 5-(2-methoxyethoxy)-1H-indole-2-carboxylate (2.0 g, 7.4 mmol) in THF (20 ml) was treated with a solution of LiOH•H$_2$O (0.62 g, 14.8 mmol) in water (10 ml). Ethanol was added until a homogenous solution formed and stirring was continued for 16 h. The reaction mixture was diluted with water (50 ml) and the organic solvents were removed in vacuo. The pH was adjusted to 4 with 1M aqueous HCl and the aqueous solution was extracted with dichloromethane. The combined organic extracts were washed with brine, dried over sodium sulfate, and concentrated in vacuo to provide 5-(2-methoxyethoxy)-1H-indole-2-carboxylic acid (1.7 g, 7.2 mmol) as a white solid. The crude acid was directly used without further purification.

Example 1

Synthesis of N-hydroxy-4-[3-(benzothiophen-2-ylcarbonylamino)prop-1-ynyl]-benzamide

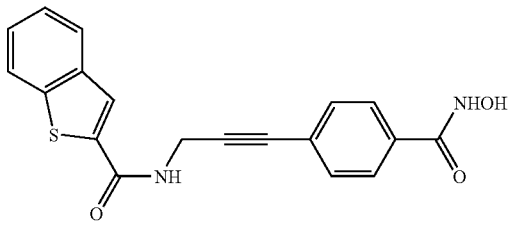

Step 1

To a solution of propargylamine (5.50 g, 100 mmol) in THF (50 ml) was added tert-butyloxycarbonyl anhydride (21.8 g, 100 mmol) in THF (50 ml) and triethylamine (16.7 ml, 120 mmol). The reaction mixture was stirred for 3 h, then diluted with ethyl acetate (200 ml), washed with 0.5M aqueous HCl (150 ml), and finally with brine (150 ml). The organic layer was dried over sodium sulfate, filtered, and concentrated in vacuo. The crude N-Boc propargylamine was directly used in the next step without further purification.

Step 2

To a solution of N-Boc propargylamine (2.07 g, 13.4 mmol), methyl 4-iodobenzoate (3.50 g, 13.4 mmol) and PdCl$_2$(PPh$_3$)$_2$ (0.938 g, 1.34 mmol) in DMF (20 ml) was added triethylamine (9.31 ml, 126 mmol). The reaction mixture was stirred for 30 min at room temperature. Cu$^{(I)}$I (0.508 g, 2.67 mmol) was added and stirring was continued for additional 16 h. The reaction mixture was diluted with ethyl acetate (250 ml), washed with 0.5M aqueous HCl (200 ml), and finally with brine (200 ml). The organic layer was dried over sodium sulfate, filtered, and concentrated in vacuo. Purification by flash chromatography over silica gel with ethyl acetate/hexane (1/4) provided methyl 4-(N-Boc-3-aminoprop-1-ynyl)benzoate (3.44 g) as highly viscous oil.

Step 3

To a solution of methyl 4-(N-Boc-3-aminoprop-1-ynyl) benzoate (3.40 g, 11.7 mmol) in THF (25 ml) was added 4M HCl/dioxane (25 ml, 100 mmol). The reaction mixture was stirred for 1 h. The formed precipitate was collected, washed with diethyl ether (200 ml) and dried in vacuo providing methyl 4-(3-aminoprop-1-ynyl)benzoate hydrochloride (2.46 g) as white solid. Alternatively, the N-Boc protected amine can be dissolved in methanol instead of THF. In this case the solvent was removed in vacuo and the precipitate was washed with diethyl ether.

Step 4

To a suspension of methyl 4-(3-aminoprop-1-ynyl)-benzoate hydrochloride (0.226 g, 1 mmol) in THF (6 ml) was added benzothiophene-2-carbonyl chloride (0.150 g, 1.0 mmol) followed by triethylamine (0.253 g, 2.5 mmol). The reaction mixture was stirred for 1 h and diluted with ethyl acetate (50 ml). The organic layer was washed with 0.5M aqueous HCl (50 ml), with saturated sodium bicarbonate solution (50 ml), and finally with brine. The organic layer was concentrated in vacuo and the crude material was directly used in the next step.

Step 5

To a solution of methyl 4-[3-(benzothiophen-2-ylcarbonylamino)prop-1-ynyl]-benzoate (0.5 mmol) in THF/methanol (10 ml/10 ml) was added 50 wt. % aqueous hydroxylamine (3 ml) followed by 1M aqueous NaOH (1 ml) adjusting the pH to 10-11. The reaction mixture was stirred for ~14 h, neutralized to pH=7-8 with 6M aqueous HCl, and concentrated in vacuo. The precipitate was collected and purified by HPLC providing the title compound as a white solid.

Example 2

Synthesis of N-hydroxy-4-[3S-(4-phenylthiazol-2-yl-carbonylamino)-but-1-ynyl]-benzamide

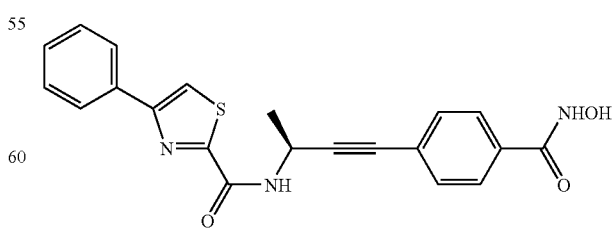

Step 1

To a solution of triphenylphosphine (5.61 g, 21.4 mmol) in anhydrous THF (40 ml) was added DIAD (4.21 ml, 21.4 mmol). The solution was stirred until a white precipitate was formed (2 to 10 min). After additional 60 min, a solution of di-tert-butyliminodicarboxylate (3.10 g, 14.3 mmol) and (R)-3-butyn-2-ol (1.0 g, 14.3 mmol) in THF (25 ml) was added and stirring was continued for 16 h. The reaction mixture was concentrated in vacuo and purified by flash chromatography over silica gel with ethyl acetate/hexane (1/20-1/1) to give N,N-bis-Boc-1(S)-methyl-prop-2-ynylamine (0.643 g) as colorless solid.

Step 2-3

N,N-Bis-Boc-1(S)-methyl-prop-2-ynylamine was converted to methyl 4-[3(S)-amino-but-1-ynyl)-benzoate hydrochloride as described in Example 1, Step 2-3 above.

Step 4

A mixture of 4-phenyl-thiazol-2-carboxylic acid (0.205 g, 1 mmol), EDC•HCl (0.268 g, 1.4 mmol) and HOBT•H$_2$O (0.203 g, 1.5 mmol) in DMF (6 ml) was stirred for 2 h. Methyl 4-[3S-aminobut-1-ynyl)-benzoate hydrochloride (0.240 g, 1 mmol) was added followed by triethylamine (0.121 g, 1.2 mmol). The reaction mixture was stirred for 2 h, diluted with ethyl acetate (50 ml), washed with saturated aqueous sodium bicarbonate solution (50 ml), and finally with brine. The organic layer was dried over sodium sulfate and concentrated in vacuo. The crude methyl 4-[3S-(4-phenyl-thiazol-2-yl-carbonylamino)but-1-ynyl]-benzoate was converted to the title compound as described in Example 1, Step 5 above.

Proceeding as described in Example 2, Step 4 above, but substituting 4-phenyl-thiazol-2-carboxylic acid with 5-(2-N,N-dimethylamino-ethoxy)-1H-indole-2-carboxylic acid (Reference H) and methyl 4-[3S-aminobut-1-ynyl)-benzoate hydrochloride with methyl 4-(3-aminoprop-1-ynyl)benzoate hydrochloride (Example 1) provided methyl 4-[3-(5-N,N-dimethylaminoethoxyindol-2-ylcarbonylamino)prop-1-ynyl]-benzoate which was converted to N-hydroxy-4-[3-(5-N,N-dimethylaminoethoxyindol-2-ylcarbonylamino)prop-1-ynyl]-benzamide as described in Example 1, Step 5 above.

Example 3

Synthesis of N-hydroxy-4-[3-(benzothiophen-2-ylcarbonylamino)-3-methylbut-1-ynyl]-benzamide

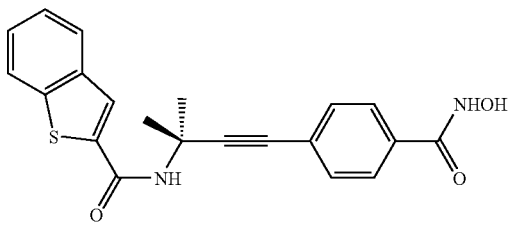

Step 1

To a solution of 2-aminoisobutyric acid (10 g, 97 mmol) in 1M aqueous NaOH (100 ml) was added tert-butyloxycarbonyl anhydride (26 g, 120 mmol) in THF (30 ml). The reaction mixture was stirred for 4 h, diluted with ethyl acetate (250 ml), washed with 0.5M aqueous HCl (200 ml), and finally with brine. The organic layer was dried over sodium sulfate and concentrated in vacuo yielding crude N-Boc-2-aminoisobutyric acid (7.3 g).

Step 2

A mixture of N-Boc-2-aminoisobutyric acid (7.22 g, 35.5 mmol), EDC•HCl (8.18 g, 42.6 mmol) and HOBT•H$_2$O (7.20 g, 42.6 mmol) in dichloromethane (100 ml) was stirred for 2 h. N,O-Dimethylhydroxylamine hydrochloride (4.16 g, 42.6 mmol) was added followed by N-methylmorpholine (15.6 ml, 142 mmol). The reaction mixture was stirred for additional 16 h and then the solvent was removed in vacuo. The residue was dissolved in ethyl acetate (200 ml), washed with 0.5M aqueous HCl (150 ml), saturated sodium bicarbonate solution (150 ml), and finally with brine. The organic layer was dried over sodium sulfate and concentrated in vacuo providing N-Boc-2-amino-N-methoxy-N-methyl-isobutyramide (2.94 g, 11.9 mmol) as colorless oil.

Step 3

To a solution of N-Boc-2-amino-N-methoxy-N-methyl-isobutyramide (2.94 g, 11.9 mmol) in diethyl ether (70 ml) at −50° C. was added slowly 1N LiAlH$_4$/diethyl ether (24 ml). Stirring was continued for 1 h and the reaction mixture was allowed to warm up to 0° C. over 2 h. The mixture was cooled to −50° C., quenched carefully with ethyl acetate (5 ml), stirred for additional 10 min, hydrolyzed with 0.5 M aqueous HCl (50 ml), and warmed up to room temperature. 1M Aqueous HCl was added until the solution became clear. The aqueous layer was extracted with diethyl ether (100 ml). The combined organic layers were finally with brine (200 ml), dried over sodium sulfate, and concentrated in vacuo providing crude N-Boc-2-amino-2-methyl-propionaldehyde (1.45 g) as colorless oil.

Step 4

To a solution of dimethyl 1-diazo-2-oxopropyl phosphonate (see Ohira, S. *Synth. Commun.* 19, 561-564, (1989)) (2.97 g, 15.5 mmol) in methanol (50 ml) at 0° C. was added potassium carbonate (1.71 g, 12.4 mmol) and slowly a solution of N-Boc-2-amino-2-methyl-propionaldehyde (1.45 g, 7.74 mmol) in methanol (5 ml). The reaction mixture was stirred at 0-10° C. for additional 6 h, diluted with diethylether (~150 ml) and with saturated aqueous ammonium chloride solution (150 ml). The organic layer was washed with saturated aqueous ammonium chloride solution (100 ml), water (100 ml), and finally with brine, dried over sodium sulfate, and concentrated in vacuo. Purification by flash chromatography over silica gel using ethyl acetate/hexane (1/10) provided N-Boc-2-amino-2-methyl-but-3-yne (1.38 g) as yellowish oil.

N-Boc-2-amino-2-methyl-but-3-yne was converted to the title compound as described in Example 1, Step 2-5 above.

Example 4

Synthesis of N-hydroxy-4-[5-((2-methoxyethoxy)-1H-indol-2-yl-carbonylamino)prop-1-ynyl]-benzamide

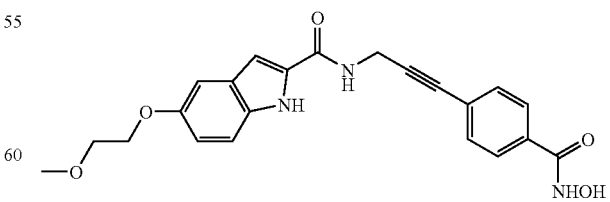

Methyl 4-(3-aminoprop-1-ynyl)benzoate hydrochloride (prepared as described in Example 1, Steps 1-3 above) and 5-(2-methoxyethoxy)-1H-indole-2-carboxylic acid (Reference I) were coupled as described in Example 6, Step 7 below, and the generated ester was converted to the title compound as described in Example 1, Step 5 above.

Example 5

N-hydroxy-4-[3-(3-(4-chlorophenyl)-ureido)prop-1-ynyl]-benzamide

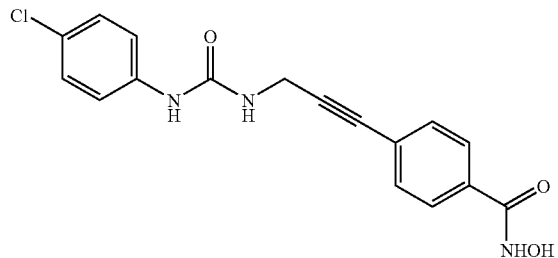

Step 1

To a solution of methyl 4-(3-aminoprop-1-ynyl)benzoate hydrochloride (see Example 1, Steps 1-3 above; 150 mg, 0.66 mmol) in THF (5 ml) was added 4-chlorophenyl isocyanate (102 mg, 0.66 mmol) and triethylamine (278 μL, 2.0 mmol). The reaction mixture was stirred for 30 min, diluted with ethyl acetate (50 ml), and sequentially washed with water (25 ml), 0.5M aqueous HCl (25 ml), saturated sodium bicarbonate (25 ml), and finally with brine (25 ml). The organic phase was dried over sodium sulfate and concentrated in vacuo to provide methyl 4-[3-(3-(4-chlorophenyl)-ureido)prop-1-ynyl]-benzoate as a white solid.

Step 2

Methyl 4-[3-(3-(4-chlorophenyl)-ureido)prop-1-ynyl]-benzoate was converted to the title compound as described in Example 1, Step 5 above.

Example 6

Synthesis of N-hydroxy-4-[1-(1H-indol-2-yl-carbonylamino)-cyclohex-1-yl-ethynyl]-benzamide

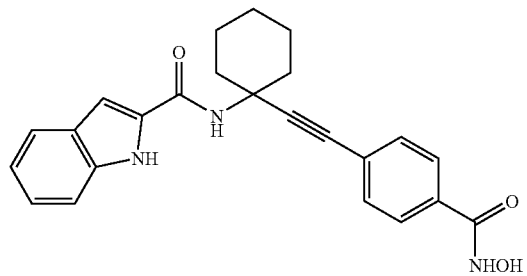

Step 1

To a suspension of 1-amino-cyclohexanecarboxylic acid (3.0 g, 21.0 mmol) in acetonitrile (20 ml) was added tetramethylammonium hydroxide pentahydrate (3.8 g, 21.0 mmol). The reaction mixture was stirred at room temperature for 1 h until most of the solids dissolved. Di-tert-butyl dicarbonate (6.9 g, 31.4 mmol) was added and the reaction mixture was stirred at room temperature for 3 days. The majority of the acetonitrile was removed in vacuo and the residue was dissolved in water (50 ml). The pH was adjusted to 7 using solid citric acid. The aqueous phase was extracted with diethyl ether and the combined ether extracts were washed with brine, dried over sodium sulfate, and concentrated in vacuo to provide crude N-Boc-1-amino-cyclohexanecarboxylic acid (3.7 g, 15.2 mmol) as a white solid which was used without further purification.

Steps 2-6

Methyl 4-(1-aminocyclohex-1-yl-ethynyl)-benzoate hydrochloride was synthesized from N-Boc-1-amino-cyclohexanecarboxylic acid according to Steps 2-4 in Example 3, and Steps 2-3 in Example 1 above.

Step 7

A solution of benzotriazol-1-yloxy-tris(dimethylamino) phosphonium hexafluorophosphate (BOP, 249 mg, 0.51 mmol) and indole-2-carboxylic acid (83 mg, 0.51 mmol) in DMF (5 ml) was treated with triethylamine (0.21 ml, 1.5 mmol). After 20 min, methyl 4-(1-amino-cyclohex-1-yl-ethynyl)-benzoate hydrochloride (150 mg, 0.51 mmol) was added and the reaction mixture was stirred for additional 16 h. The reaction mixture was diluted with ethyl acetate (50 ml) and the organic layer was washed with water (25 ml), 1M aqueous HCl (25 ml), saturated sodium bicarbonate (25 ml), and brine, dried over sodium sulfate, and concentrated in vacuo to provide crude methyl 4-[1-(1H-indol-2-yl-carbonylamino)-cyclohex-1-yl-ethynyl]-benzoate which was used without further purification.

Step 8

Methyl 4-[1-(1H-indol-2-yl-carbonylamino)-cyclohex-1-ylethynyl]-benzoate was converted to the title compound as described in Example 1, Step 5 above.

Example 7

Synthesis of N-hydroxy-4-[4-(1H-indol-2-yl-carbonylamino)piperidin-4-yl-ethynyl]-benzamide

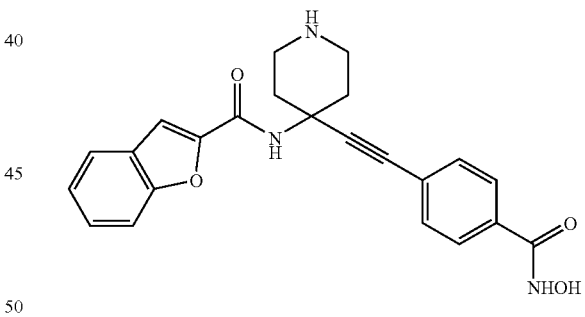

Steps 1-6

1-N-Boc-4,4-amino-piperidinylcarboxylic acid was converted to methyl 4-(4-amino-piperidin-4-ylethynyl)-benzoate dihydrochloride salt as described in Example 1, Steps 1-6 above.

Step 7

A solution of methyl 4-(4-aminopiperidin-4-ylethynyl)-benzoate dihydrochloride (791 mg, 2.4 mmol) in THF (15 ml) was treated with triethylamine (1.3 ml, 9.6 mmol) and di-tert-butyl dicarbonate (521 mg, 2.4 mmol). After 1 h, the reaction mixture was diluted with ethyl acetate (150 ml) and the organic layer was washed with water and brine, dried over sodium sulfate, and concentrated in vacuo to provide N-Boc methyl 4-(4-amino-piperidin-4-ylethynyl)-benzoate (930 mg, 2.6 mmol) as yellowish foam which was used in the next step without further purification.

Step 8

N-Boc methyl 4-(4-aminopiperidin-4-ylethynyl)-benzoate was converted to N-Boc methyl 4-[4-(benzofuran-2-yl-carbonylamino)piperidin-4-ylethynyl]-benzoate as describe in Example 6, Step 7 above.

Step 9

N-Boc methyl 4-[4-(benzofuran-2-ylcarbonylamino)piperidin-4-ylethynyl]benzoate was converted to methyl 4-[4-(benzofuran-2-ylcarbonylamino)piperidin-4-ylethynyl]benzoate hydrochloride salt as described in Example 1, Step 3 above.

Step 10

Methyl 4-[4-(benzofuran-2-ylcarbonylamino)piperidin-4-ylethynyl]benzoate hydrochloride was converted to the title compound as described in Example 1, Step 5 above.

Example 8

Synthesis of N-hydroxy-4-[4-(1H-indol-2-yl-carbonylamino)-1-(2,2,2-trifluoro-ethyl)-piperidin-4-yl-ethynyl]-benzamide

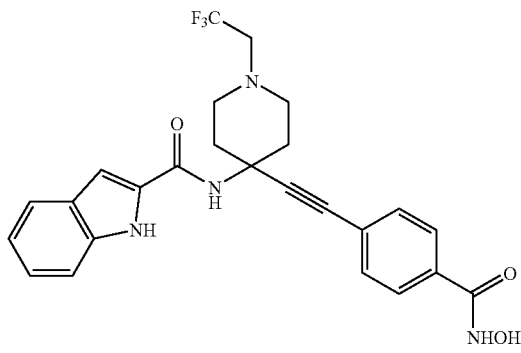

Steps 1-9

Methyl 4-[4-(1H-indol-2-ylcarbonylamino)piperidin-4-ylethynyl]benzoate hydrochloride was synthesized according to Example 7, Steps 1-9 above.

Step 10

Methyl 4-[4-(1H-indol-2-ylcarbonylamino)piperidin-4-ylethynyl]benzoate hydrochloride (207 mg, 0.47 mmol) in dichloromethane (5 ml) was treated with 2,6-lutidine (164 μl, 1.4 mmol), followed by (2,2,2-trifluoroethyl)phenyliodonium triflate (see Montanari, V.; Resnati, G. *Tetrahedron Lett.* 35, 8015, (1994)) (207 mg, 0.47 mmol). The reaction mixture was stirred at room temperature for 16 h and concentrated in vacuo. The crude methyl 4-[4-(1H-indol-2-ylcarbonylamino)-1-(2,2,2-trifluoroethyl)piperidin-4-yl-ethynyl]benzoate was used in the next step without further purification.

Step 11

Methyl 4-[4-(1H-indol-2-ylcarbonylamino)-1-(2,2,2-trifluoroethyl)piperidin-4-yl-ethynyl]benzoate was converted to the title compound as described in Example 1, Step 5 above.

Proceeding as described in Working Examples above, the following compounds of the present invention were prepared.

Table I:

Compound 1: N-hydroxy-4-[3-(3-phenylacryloylamino)prop-1-ynyl]-benzamide.

$^1$H NMR (400 MHz, DMSO-$d_6$) δ 11.28 (s, 1H), 9.08 (s, 1H), 9.67 (t, J=5.5 Hz, 1H), 7.74 (d, J=8.5 Hz, 2H), 7.58 (d, J=6.9 Hz, 2H), 7.50 (d, J=8.4 Hz, 2H), 7.49 (d, J=15.9 Hz, 1H), 7.42 (m, 3H), 6.66 (d, J=15.8 Hz, 1H), 4.29 (d, J=5.5 Hz, 2H). EM (calc.): 320.1; MS (ESI) m/e (M+1H)$^+$: 321.0, (M−1H)$^-$: 319.1.

Compound 2: N-hydroxy-4-[3-(4-phenylthiazol-2-ylcarbonylamino)prop-1-ynyl]-benzamide.

$^1$H NMR (400 MHz, DMSO-$d_6$): δ 11.29 (s, 1H), 9.50 (t, J=6.3 Hz, 1H), 8.47 (s, 1H), 8.12 (d, J=7.2 Hz, 2H), 7.75 (d, J=8.3 Hz, 2H), 7.52 (m, 4H), 7.42 (m, 1H), 4.41 (d, J=5.9 Hz, 2H). EM (calc.): 377.08; MS (ESI) m/e (M+1H)$^+$: 378.0 (M−1H)$^-$: 376.0.

Compound 3: N-hydroxy-4-[3S-(3-phenylacryloylamino)-but-1-ynyl]-benzamide.

$^1$H NMR (400 MHz, DMSO-d6): δ 11.03 (s, 1H), 9.11 (br s, 1H), 8.75 (d, J=7.8 Hz, 1H), 7.75 (d, J=8.3 Hz, 2H), 7.59 (d, J=7.9 Hz, 2H), 7.51 (d, J=8.3 Hz, 2H), 7.46-7.38 (m, 3H), 7.43 (d, J=15.5 Hz, 1H), 6.66 (d, J=15.7 Hz, 1H), 1.49 (d, J=6.7 Hz, 3H). EM (calc.): 334.1; MS (ESI) m/e (M+1H)$^+$: 335.2, (M−1H)$^-$: 333.1.

Compound 4: N-hydroxy-4-[3-(4-methoxyquinolin-2-ylcarbonylamino)prop-1-ynyl]-benzamide.

$^1$H NMR (400 MHz, DMSO-$d_6$): δ 11.28 (s, 1H), 9.41 (t, J=6.5 Hz, 1H), 9.10 (s, 1H), 8.22 (dd, J$_1$=8.3 Hz, J$_2$=0.9 Hz, 1H), 8.10 (d, J=8.3 Hz, 1H), 7.88 (pseudo t, J=7.4 Hz, 1H), 7.74 (d, J=8.7 Hz, 2H), 7.70 (pseudo t, J=6.7 Hz, 1H), 7.65 (s, 1H), 4.45 (d, J=6.1 Hz, 2H), 4.17 (s, 3H). EM (calc.): 375.1; MS (ESI) m/e (M+1H)$^+$: 375.8, (M−1H)$^-$: 374.0.

Compound 5: N-hydroxy-4-{3-[2-(4-aminomethylphenyl)oxazol-5-ylcarbonylamino)-prop-1-ynyl]-benzamide.

$^1$H NMR (400 MHz, DMSO-$d_6$): δ 11.31 (s, 1H), 10.25 (s, 1H), 8.94 (t, J=5.9 Hz, 1H), 8.82 (s, 1H), 8.47 (br s, 3H), 8.09 (d, J=8.3 Hz, 2H), 7.75 (d, J=8.2 Hz, 2H), 7.71 (d, J=8.3 Hz, 2H), 7.51 (d, J=8.3 Hz, 2H), 4.36 (d, J=5.9 Hz, 2H), 4.14 (q, J=5.4 Hz, 2H). EM (calc.): 390.1; MS (ESI) m/e (M+1H)$^+$: 391.2, (M−1H)$^-$: 389.3.

Compound 6: N-hydroxy-4-[3S-(4-phenylthiazol-2-ylcarbonylamino)but-1-ynyl]-benzamide.

$^1$H NMR (400 MHz, DMSO-$d_6$): δ 11.30 (s, 1H), 9.88 (d, J=8.7 Hz, 1H), 9.11 (s, 1H), 8.47 (s, 1H), 8.14 (d, J=8.6 Hz, 2H), 7.75 (d, J=8.6 Hz, 2H), 7.51 (m, 5H), 7.42 (m, 1H), 5.19 (pseudo p, J=7.1 Hz, 1H), 1.62 (d, J=7.1 Hz, 3H). EM (calc.): 391.1; MS (ESI) m/e (M+1H)$^+$: 392.2, (M−1H)$^-$: 390.2.

Compound 7: N-hydroxy-4-[3-(phenylcarbonylamino)prop-1-ynyl]-benzamide.

$^1$H NMR (400 MHz, DMSO-$d_6$): δ 11.29 (s, 1H), 9.07 (t, J=5.9 Hz, 11H), 7.91 (d, J=8.1 Hz, 2H), 7.75 (d, J=8.7 Hz, 2H), 7.48-7.59 (m, 5H), 4.38 (d, J=5.5 Hz, 2H). EM (calc.): 294.1; MS (ESI) m/e (M+1H)$^+$: 295.1, (M−1H)$^-$: 293.0.

Compound 8: N-hydroxy-4-{3-[methyl-(3-phenylacryloyl)amino]prop-1-ynyl}-benzamide.

$^1$H NMR (400 MHz, DMSO-$d_6$) $^1$H NMR (400 MHz, DMSO-$d_6$) δ 11.65 (s, 1H), 11.30 (s, 1H), 9.10 (s, 1H), 7.75 (d, J=7.6 Hz, 4H), 7.58 (s, 1H), 7.54 (t, J=4.4 Hz, 3H), 7.43 (m, 4H), 7.27 (m, 1H), 4.56 (s, 2H). EM (calc.): 334.1; MS (ESI) m/e (M+1H)$^+$: 335.1, (M−1H)$^-$: 333.1.

Compound 9: N-hydroxy-4-{3-[methyl-(4-phenylthiazol-2-ylcarbonyl)amino]prop-1-ynyl}-benzamide.

$^1$H NMR (400 MHz, DMSO-$d_6$) δ 11.29 (d, J=7.2 Hz, 11H), 9.10 (br, s 1H), 8.49 (s, 1H), 8.06 (d, J=7.2 Hz, 11H), 8.02 (d, J=7.2 Hz, 1H), 7.75 (t, J=8.0 Hz, 1H), 7.58 (d, J=8.0 Hz, 11H), 7.49 (m, 3H), 7.41 (t, J=7.6 Hz, 1H), 4.69 (s, 2H), 3.45 (s, 3H). EM (calc.): 391.1; MS (ESI) m/e (M+1H)$^+$: 392.3, (M−1H)$^-$: 390.2.

Compound 10: N-hydroxy-4-[3-(benzothiophen-2-ylcarbonylamino)prop-1-ynyl]-benzamide.

$^1$H NMR (400 MHz, DMSO-d$_6$) δ 11.27 (br s, 1H), 9.35 (t, J=5.5 Hz, 11H), 9.08 (br s, 1H), 8.15 (s, 1H), 8.03 (d, J=7.4 Hz, 1H), 7.96 (d, J=8.7 Hz, 1H), 7.74 (d, J=8.6 Hz, 2H), 7.52 (d, J=8.3 Hz, 2H), 7.56 (m, J$_1$=1.5 Hz, J$_2$=7.3 Hz, 2H), 4.38 (d, J=5.5 Hz, 2H). EM (calc.): 350.1; MS (ESI) m/e (M+1H)$^+$: 351.0, (M−1H)$^−$: 348.9.

Compound 11: N-hydroxy-4-[3-(5-chlorobenzofuran-2-ylcarbonylamino)prop-1-ynyl]-benzamide.

$^1$H NMR (400 MHz, DMSO-d$_6$): δ 11.29 (s, 1H), 9.40 (t, J=5.4 Hz, 1H), 9.10 (s, 1H), 7.91 (d, J=2.0 Hz, 1H), 7.75 (d, J=8.5 Hz, 2H), 7.73 (m, 1H), 7.62 (d, J=0.7 Hz, 1H), 7.52 (d, J=8.6 Hz, 2H), 7.51 (m, 1H), 4.38 (d, J=5.5 Hz, 2H). EM (calc.): 368.1; MS (ESI) m/e (M+1H)$^+$: 369.0, (M−1H)$^−$: 367.1.

Compound 12: N-hydroxy-4-[3-(5-indol-2-ylcarbonylamino)prop-1-ynyl]-benzamide.

$^1$H NMR (400 MHz, DMSO-d$_6$): δ 11.87 (s, 1H), 11.29 (s, 1H), 9.16 (t, J=5.5 Hz, 1H), 9.10 (s, 1H), 7.75 (d, J=8.5 Hz, 2H), 7.74 (m, 1H), 7.53 (d, J=8.2 Hz, 2H), 7.45 (d, J=8.5 Hz, 1H), 7.21 (dd, J$_1$=8.5 Hz, J$_2$=1.9 Hz, 1H), 7.19 (d, J=1.5 Hz, 1H), 4.41 (d, J=5.6 Hz, 2H). EM (calc.): 367.1; MS (ESI) m/e (M+1H)$^+$: 368.0, (M−1H)$^−$: 366.3.

Compound 13: N-hydroxy-4-[3-(benzofuran-2-ylcarbonylamino)prop-1-ynyl]-benzamide.

$^1$H NMR (400 MHz, DMSO-d$_6$): δ 11.29 (s, 1H), 9.33 (t, J=5.3 Hz, 1H), 9.10 (s, 1H), 7.81 (d, J=7.4 Hz, 1H), 7.75 (d, J=8.6 Hz, 2H), 7.63 (s, 1H), 7.52 (d, J=8.1 Hz, 2H), 7.49 (m, 1H), 7.36 (t, J=6.7 Hz, 1H), 4.38 (d, J=5.4 Hz, 2H). EM (calc.): 334.1; MS (ESI) m/e (M+1H)$^+$: 335.1, (M−1H)$^−$: 333.1.

Compound 14: N-hydroxy-4-[3S-(benzothiophen-2-ylcarbonylamino)but-1-ynyl]-benzamide.

$^1$H NMR (400 MHz, DMSO-d$_6$): δ 11.30 (s, 1H), 9.32 (d, J=7.4 Hz, 1H), 9.10 (s, 1H), 8.22 (s, 1H), 8.01 (dd, J$_1$=7.0 Hz, J$_2$=7.1 Hz, 2H), 7.76 (d, J=8.3 Hz, 2H), 7.53 (d, J=8.3 Hz, 2H), 7.48 (m, 2H), 5.14 (pseudo p, J=7.4 Hz, 1H), 1.58 (d, J=7.1 Hz, 3H). EM (calc.): 364.1; MS (ESI) m/e (M+1H)$^+$: 365.3, (M−1H)$^−$: 363.1.

Compound 15: N-hydroxy-4-[3-(indol-2-ylcarbonylamino)prop-1-ynyl]-benzamide.

$^1$H NMR (400 MHz, DMSO-d$_6$) δ 11.62 (s, 1H), 11.26 (s, 1H), 9.03 (t, J=5.6 Hz, 1H), 7.71 (d, J=8.4 Hz, 2H), 7.60 (d, J=8.1 Hz, 1H), 7.49 (d, J=8.3 Hz, 2H), 7.41 (d, J=8.8 Hz, 1H), 7.16 (m, 2H), 7.02 (t, J=7.8 Hz, 1H), 4.38 (d, J=5.6 Hz, 2H). EM (calc.): 333.1; MS (ESI) m/e (M+1H)$^+$: 334.0, (M−1H)$^−$: 332.1.

Compound 16: N-hydroxy-4-{3-[3-(2,2,2-trifluoroethyloxymethyl)benzofuran-2-yl-carbonylamino]prop-1-ynyl}-benzamide.

$^1$H NMR (400 MHz, DMSO-d$_6$): δ 11.29 (s, 1H), 9.39 (t, J=5.9 Hz, 1H), 9.10 (s, 1H), 7.86 (d, J=7.7 Hz, 1H), 7.75 (d, J=8.5 Hz, 21H), 7.68 (d, J=8.1 Hz, 1H), 7.56 (m, 1H), 7.52 (d, J=8.1 Hz, 2H), 7.40 (t, J=7.3 Hz, 1H), 5.29 (s, 2H), 4.37 (d, J=6.0 Hz, 2H), 4.21 (q, J=9.7 Hz, 2H). EM (calc.): 446.1; MS (ESI) m/e (M+1H)$^+$: 447.4, (M−1H)$^−$: 445.3.

Compound 17: N-hydroxy-4-[3-(benzthiazol-2-ylcarbonylamino)prop-1-ynyl]-benzamide.

$^1$H NMR (400 MHz, DMSO-d$_6$):δ 11.30 (s, 1H), 9.75 (t, J=5.8 Hz, 1H), 9.10 (s, 1H), 8.26 (d, J=8.6 Hz, 1H), 8.17 (d, J=8.6 Hz, 1H), 7.75 (d, J=8.3 Hz, 2H), 7.65 (m, 2H), 7.52 (d, J=8.2 Hz, 2H), 4.40 (d, J=5.5 Hz, 2H). EM (calc.): 351.1; MS (ESI) m/e (M+1H)$^+$: 351.9, (M−1H)$^−$: 350.0.

Compound 18: N-hydroxy-4-{3-[(methyl-(5-fluorobenzothiophen-2-ylcarbonyl)-amino]prop-1-ynyl}-benzamide.

$^1$H NMR (400 MHz, DMSO-d$_6$):δ 11.30 (s, 1H), 9.67 (t, J=5.2 Hz, 1H), 9.11 (s, 1H), 8.42 (d, J=7.2 Hz, 1H), 8.41 (s, 1H), 7.88 (d, J=7.4 Hz, I1H), 7.75 (d, J=8.2 Hz, 2H), 7.67 (t, J=8.0 Hz, 1H), 7.55 (d, J=8.2 Hz, 2H), 4.44 (d, J=5.2 Hz, 2H). EM (calc.): 418.1; MS (ESI) m/e (M+1H)$^+$: 419.2, (M−1H)$^−$: 417.1.

Compound 19: N-hydroxy-4-[3-(benzimidazol-2-ylcarbonylamino)prop-1-ynyl]-benzamide.

$^1$H NMR (400 MHz, DMSO-d$_6$):δ 11.31 (br s, 1H), 9.57 (t, J=5.8 Hz, 1H), 7.75 (d, J=8.3 Hz, 2H), 7.68 (dd, J$_1$=3.1 Hz, J$_2$=5.8 Hz, 2H), 7.52 (d, J=8.2 Hz, 2H), 7.35 (dd, J$_1$=3.1 Hz, J$_2$=5.9 Hz, 2H), 4.47 (d, J=5.9 Hz, 2H). EM (calc.): 334.1; MS (ESI) m/e (M+1H)$^+$: 335.0, (M−1H)$^−$: 333.1.

Compound 20: N-hydroxy-4-{3-[methyl-(benzothiophen-2-ylcarbonyl)amino]prop-1-ynyl}-benzamide.

$^1$H NMR (400 MHz, DMSO-d$_6$):δ 11.32 (s, I1H), 9.12 (s, 1H), 8.05 (dd, J$_1$=2.1 Hz, J$_2$=8.6 Hz, 1H), 7.98 (dd, J$_1$=2.4 Hz, J$_2$=6.3 Hz, 1H), 7.78 (d, J=8.3 Hz, 2H), 7.59 (d, J=8.3 Hz, 2H), 7.48 (m, 2H), 4.68 (s, 2H), 3.36 (s, 3H). EM (calc.): 364.1; MS (ESI) m/e (M+1H)$^+$: 365.2, (M−1H)$^−$: 363.1.

Compound 21: N-hydroxy-4-[3-(5-fluorobenzothiophen-2-ylcarbonylaminoprop-1-ynyl]-benzamide.

$^1$H NMR (400 MHz, DMSO-d$_6$): δ 11.29 (s, 1H), 9.44 (t, J=5.5 Hz, 1H), 9.14 (s, 1H), 8.13 (s, 1H), 8.10 (dd, J$_1$=5.1 Hz, J$_2$=9.0 Hz, 1H), 7.84 (dd, J$_1$=2.7 Hz, J$_2$=9.4 Hz, 1H), 7.75 (d, J=8.3 Hz, 2H), 7.53 (d, J=8.5 Hz, 2H), 7.39 (td, J$_1$=2.7 Hz, J$_2$=9.0 Hz, 1H), 4.40 (d, J=5.5 Hz, 2H). EM (calc.): 368.1; MS (ESI) m/e (M+1H)$^+$: 369.0, (M−1H)$^−$: 367.2.

Compound 22: N-hydroxy-4-[3-(3-N,N-dimethylaminomethylbenzofuran-2-ylcarbonylamino)prop-1-ynyl]-benzamide hydrochloride.

$^1$H NMR (400 MHz, DMSO-d$_6$):δ 11.34 (br s, 1H), 10.11 (br s, 2H), 9.71 (t, J=5.6 Hz, 1H), 8.11 (d, J=7.5 Hz, 1H), 7.76 (d, J=8.2 Hz, 2H), 7.74 (s, 1H), 7.61 (td, J$_1$=1.2 Hz, J$_2$=7.0 Hz, 1H), 7.51 (d, J=8.2 Hz, 2H), 7.47 (d, J=7.4 Hz, 1H), 4.82 (s, 2H), 4.42 (d, J=5.4 Hz, 2H), 2.88 (s, 6H). EM (calc.): 391.2; MS (ESI) m/e (M+1H)$^+$: 392.2, (M−1H)$^−$: 390.3.

Compound 23: N-hydroxy-4-{3-[1-(2-N,N-dimethylaminoethyl)benzimidazol-2-yl-carbonylamino]prop-1-ynyl}benzamide hydrochloride.

$^1$H NMR (400 MHz, DMSO-d$_6$):δ 11.26 (s, 1H), 10.12 (s, 1H), 9.64 (t, J=5.9 Hz, 1H), 7.85 (d, J=8.3 Hz, 1H), 7.78 (d, J=7.9 Hz, 1H), 7.72 (d, J=8.8 Hz, 2H), 7.48 (d, J=8.1 Hz, 2H), 7.44 (m, 1H), 7.37 (m, 1H), 5.04 (t, J=7.1 Hz, 2H), 4.36 (d, J=5.9 Hz, 2H), 3.55 (pseudo q, J=6.0 Hz, 2H), 2.90 (d, J=4.6 Hz, 6H). EM (calc.): 405.2; MS (ESI) m/e (M+1H)$^+$: 406.0, (M−1H)$^−$: 404.3.

Compound 24: N-hydroxy-4-[3-(4-methoxybenzofuran-2-ylcarbonylamino)prop-1-ynyl]-benzamide.

$^1$H NMR (400 MHz, DMSO-d$_6$) δ 11.26 (s, 1H), 9.08 (s, 1H), 8.88 (t, J=5.2 Hz, 1H), 8.43 (s, 1H), 7.73 (d, J=8.1 Hz, 2H), 7.52 (d, J=8.1 Hz, 2H), 7.36 (t, J=8.1 Hz, 1H), 7.30 (d, J=8.2 Hz, 1H), 6.96 (d, J=7.9 Hz, 1H), 4.41 (d, J=5.2 Hz, 2H), 3.99 (s, 3H). EM (calc.): 364.1; MS (ESI) m/e (M+1H)$^+$: 365.1, (M−1H)$^−$: 363.2.

Compound 25: N-hydroxy-4-[3-(4-N,N-dimethylaminoethoxybenzofuran-2-ylcarbonylamino)-prop-1-ynyl]-benzamide hydrochloride.

$^1$H NMR (400 MHz, DMSO-d$_6$) δ 11.30 (s, 1H), 9.80 (br s, 1H), 9.12 (s, 1H), 8.41 (s, 1H), 7.76 (d, J=8.4 Hz, 2H), 7.69 (d, J=8.3 Hz, 1H), 7.53 (d, J=8.3 Hz, 2H), 7.47 (d, J=8.6 Hz, 1H), 7.39 (t, J=8.2 Hz, 1H), 7.36 (t, J=8.2 Hz, 1H), 7.00 (d, J=7.8 Hz, 1H), 4.30 (t, J=4.9 Hz, 2H), 4.42 (d,

J=5.4 Hz, 2H), 3.58 (m, 2H), 2.91 (d, J=4.8 Hz, 6H). EM (calc.): 421.2; MS (ESI) m/e (M+1H)⁺: 422.2, (M−1H)⁻: 420.2.

Compound 26: N-hydroxy-4-[3-(4-methoxyindol-2-yl-carbonylamino)prop-1-ynyl]-benzamide.

¹H NMR (400 MHz, DMSO-$d_6$) δ 11.61 (s, 1H), 11.25 (s, 1H), 9.06 (s, 1H), 8.96 (t, J=5.6 Hz, 1H), 7.71 (d, J=8.4 Hz, 2H), 7.49 (d, J=8.3 Hz, 2H), 7.22 (s, 1H), 7.08 (t, J=8.0 Hz, 1H), 6.99 (d, J=8.3 Hz, 1H), 6.49 (d, J=7.6 Hz, 1H), 4.36 (d, J=5.5 Hz, 2H), 3.87 (s, 3H). EM (calc.): 363.1; MS (ESI) m/e (M+1H)⁺: 364.4, (M−1H)⁻: 362.3.

Compound 27: N-hydroxy-4-[3-(4-N,N-dimethylamino-ethoxyindol-2-yl-carbonyl-amino)prop-1-ynyl]-benzamide hydrochloride.

¹H NMR (400 MHz, DMSO-$d_6$) δ 11.74 (s, 1H), 10.49 (br s, 1H), 10.23 (s, 1H), 9.06 (t, J=5.6 Hz, 1H), 7.74 (d, J=6.8 Hz, 2H), 7.51 (d, J=8.5 Hz, 2H), 7.30 (s, 1H), 7.13 (t, J=8.2 Hz, 1H), 7.07 (d, J=8.3 Hz, 1H), 6.58 (d, J=7.8 Hz, 1H), 4.50 (t, J=4.8 Hz, 2H), 4.38 (d, J=5.5 Hz, 2H), 3.59 (pseudo q, J=4.9 Hz, 2H), 2.93 (d, J=4.8 Hz, 6H). EM (calc.): 420.2; MS (ESI) m/e (M+1H)⁺: 421.1, (M−1H)⁻: 419.4.

Compound 28: N-hydroxy-4-[3-(5-methoxyindol-2-yl-carbonylamino)prop-1-ynyl]-benzamide.

¹H NMR (400 MHz, DMSO-$d_6$) δ 11.47 (s, 1H), 11.25 (s, 1H), 9.10 (br s, 1H), 8.98 (s, 1H), 7.71 (d, J=7.6 Hz, 2H), 7.49 (d, J=7.7 Hz, 2H), 7.30 (d, J=8.7 Hz, 1H), 7.07 (s, 1H), 6.82 (d, J=9.0 Hz, 1H), 4.37 (s, 2H), 3.75 (s, 3H). EM (calc.): 363.1; MS (ESI) m/e (M+1H)⁺: 364.3, (M−1H)⁻: 362.3.

Compound 29: N-hydroxy-4-[3-(5-N,N-dimethylamino-ethoxyindol-2-ylcarbonyl-amino)-prop-1-ynyl]-benzamide hydrochloride.

¹H NMR (400 MHz, DMSO-$d_6$) δ 11.59 (s, 1H), 11.29 (s, 1H), 9.85 (s, 1H), 9.10 (s, 1H), 9.05 (t, J=5.5 Hz, 1H), 7.74 (d, J=8.3 Hz, 2H), 7.51 (d, J=8.3 Hz, 2H), 7.37 (d, J=8.8 Hz, 1H), 7.21 (d, J=2.4 Hz, 1H), 7.13 (d, J=1.7 Hz, 1H), 6.93 (dd, $J_1$=2.4 Hz, $J_2$=8.9 Hz, 1H), 4.40 (d, J=5.5 Hz, 2H), 4.33 (t, J=4.8 Hz, 2H), 3.52 (t, J=4.8 Hz, 2H), 2.88 (s, 6H). EM (calc.): 420.2; MS (ESI) m/e (M+1H)⁺: 421.0, (M−1H)⁻: 419.2.

Compound 30: N-hydroxy-4-{3-[3-(2-methoxyethy-loxymethyl)benzofuran-2-ylcarbonyl-amino]prop-1-ynyl}benzamide.

¹H NMR (400 MHz, DMSO-$d_6$) δ 11.27 (s, 1H), 9.27 (t, J=4.4 Hz, 1H), 7.89 (d, J=6.4 Hz, 1H), 7.73 (d, J=7.2 Hz, 2H), 7.64 (d, J=6.4 Hz, 1H), 7.52-7.49 (m, 3H), 7.36 (pseudo t, J=6.4 Hz, 1H), 5.07 (s, 2H), 4.34 (d, J=4.4 Hz, 2H), 3.61 (ddd, $J_1$=3.2 Hz, $J_2$=4.0 Hz, $J_3$=5.2 Hz, 2H), 3.49 (ddd, $J_1$=2.8 Hz, $J_2$=3.6 Hz, $J_3$=4.8 Hz, 2H), 3.24 (s, 3H). EM (calc): 422.15; MS (ESI) m/e (M+1H)⁺: 423.2, (M−1H)⁻: 421.3.

Compound 31: N-hydroxy-4-{3-[3-(2-methoxyethyloxy) indol-2-ylcarbonylamino]prop-1-ynyl}benzamide.

¹H NMR (400 MHz, DMSO-$d_6$) δ 11.28 (s, 1H), 9.10 (br s, 1H), 8.95 (t, J=5.6 Hz, 1H), 8.91 (br s, 1H), 7.75 (d, J=8.4 Hz, 2H), 7.51 (d, J=8.4 Hz, 2H), 7.37 (d, J=8.9 Hz, 1H), 6.97 (s, 1H), 6.90 (d, J=2.4 Hz, 1H), 6.80 (dd, $J_1$=2.4 Hz, $J_2$=8.9 Hz, 1H), 4.66 (t, J=5.6 Hz, 2H), 4.34 (d, J=5.5 Hz, 2H), 3.60 (t, J=5.5 Hz, 2H), 3.18 (s, 3H). EM (calc.): 407.4; MS (ESI) m/e (M+1H)⁺: 408.2, (M−1H)⁻: 406.3.

Compound 32: N-hydroxy-4-[3-(5-tetrahydropyran-4-yloxybenzofuran-2-yl-carbonylamino)prop-1-ynyl]benzamide.

¹H NMR (400 MHz, DMSO-$d_6$) δ 11.28 (s, 1H), 9.28 (t, J=5.6 Hz, 1H), 8.10 (s, 1H), 7.75 (d, J=8.3 Hz, 2H), 7.57 (d, J=9.1 Hz, 1H), 7.52 (d, J=8.3 Hz, 2H), 7.38 (d, J=2.5 Hz, 1H), 7.11 (dd, $J_1$=2.6 Hz, $J_2$=9.0 Hz, 1H), 4.60 (pseudo sept, J=4.0 Hz, 1H), 4.37 (d, J=5.6 Hz, 2H), 3.89 (dt, $J_1$=11.5 Hz, $J_2$=4.2 Hz, 2H), 3.51 (td, $J_1$=9.5 Hz, $J_2$=2.8 H, 2H), 2.02 (m, 2H), 1.62 (m, 2H). EM (calc.): 434.4; MS (ESI) m/e (M+1H)⁺: 435.3, (M−1H)⁻: 433.4.

Compound 33: N-hydroxy-4-{3-[5-(2-pyrrolidin-1-ylethoxy)benzofuran-2-yl-carbonyl-amino]prop-1-ynyl}benzamide hydrochloride.

¹H NMR (400 MHz, DMSO-$d_6$) δ 11.29 (s, 1H), 9.94 (br s, 1H), 9.30 (t, J=5.5 Hz, 1H), 9.10 (s, 1H), 7.75 (d, J=8.4 Hz, 2H), 7.64 (d, J=9.0 Hz, 1H), 7.59 (s, 1H), 7.52 (d, J=8.4 Hz, 2H), 7.39 (d, J=2.6 Hz, 1H), 7.17 (dd, $J_1$=2.6 Hz, $J_2$=9.0 Hz, 1H), 4.37 (d, J=5.7 Hz, 2H), 4.38 (m, 2H), 3.64 (m, 3H), 3.17 (m, 2H), 2.07 (m, 2H), 1.92 (m, 2H). EM (calc.): 447.5; MS (ESI) m/e (M+1H)⁺: 448.0, (M−1H)⁻: 446.4.

Compound 34: N-hydroxy-4-{3-[5-(2-methoxyethyloxy) benzofuran-2-yl-carbonylamino]-prop-1-ynyl}benzamide.

¹H NMR (400 MHz, DMSO-$d_6$) δ 11.28 (s, 1H), 9.27 (t, J=5.6, 1H), 9.10 (s, 1H), 7.74 (d, J=8.4 Hz, 2H), 7.58 (d, J=9.1 Hz, 1H), 7.54 (s, 1H), 7.52 (d, J=8.4 Hz, 2H), 7.30 (d, J=2.6 Hz, 1H), 7.10 (dd, $J_1$=2.7 Hz, $J_2$=9.0 Hz, 1H), 4.37 (d, J=5.6 Hz, 2H), 4.15 (t, J=4.8 Hz, 2H), 3.71 (t, J=4.8 Hz, 2H), 3.34 (s, 3H). EM (calc.): 408.4; MS (ESI) m/e (M+1H)⁺: 409.2, (M−1H)⁻: 407.0.

Compound 35: N-hydroxy-4-{3-[4-(N,N-dimethylamino-ethyloxy)quinolin-2-ylcarbonyl-amino]prop-1-ynyl }benzamide hydrochloride.

¹H NMR (400 MHz, DMSO-$d_6$) δ 11.30 (s, 1H), 10.31 (br s, 1H), 9.45 (t, J=6.0 Hz, 1H), 8.45 (d, J=9.3 Hz, 1H), 8.11 (d, J=8.1 Hz, 1H), 7.91 (t, J=8.4 Hz, 1H), 7.74 (d, J=8.4 Hz, 2H), 7.73 (t, J=8.4 Hz, 1H), 7.69 (s, 1H), 7.51 (d, J=8.4 Hz, 2H), 4.78 (t, J=4.4 Hz, 2H), 4.45 (d, J=6.0 Hz, 2H), 3.73 (pseudo q, J=4.8 Hz, 2H), 2.95 (d, J=4.9 Hz, 6H). EM (calc.): 432.5; MS (ESI) m/e (M+1H)⁺: 433.5, (M−1H)⁻: 431.4.

Compound 36: N-hydroxy-4-{3-[5-(1-(2,2,2-trifluoroet-hyl)piperidin-4-yloxy)-benzofuran-2-ylcarbonylamino] prop-1-ynyl}benzamide.

¹H NMR (400 MHz, DMSO-$d_6$) δ 11.29 (br s, 1H), 9.31 (t, J=5.6 Hz, 1H), 7.75 (d, J=8.4 Hz, 2H), 7.59 (d, J=9.0 Hz, 1H), 7.55 (s, 1H), 7.51 (d, J=8.3 Hz, 2H), 7.39 (d, J=2.5 Hz, 1H), 7.13 (dd, $J_1$=2.5 Hz, $J_2$=9.0 Hz, 1H), 4.59 (br s, 1H), 4.37 (d, J=5.6 Hz, 2H), 3.25 (m, 3H), 3.06 (m, 2H), 2.16 (m, 2H), 1.93 (m, 2H). EM (calc.): 515.5; MS (ESI) m/e (M+1H)⁺: 516.5, (M−1H)⁻: 514.2.

Compound 37: N-hydroxy-4-{3-[5-(1-cyclopropylpiperi-din-4-yloxy)benzofuran-2-yl-carbonylamino]prop-1-ynyl}benzamide hydrochloride.

¹H NMR (400 MHz, DMSO-$d_6$) δ 11.30 (s, 1H), 10.38 (br s, 1H), 9.33 (t, J=5.8 Hz, 1H), 9.11 (s, 1H), 7.75 (d, J=8.3 Hz, 2H), 7.62 (t, J=9.3 Hz, 1H), 7.56 (d, J=4.8 Hz, 1H), 7.52 (d, J=8.3 Hz, 2H), 7.43 (d, J=17.2 Hz, 1H), 7.22, 7.13 (d, J=8.7 Hz, 1H), 4.79, 4.60 (br s, 1H), 4.37 (d, J=5.2 Hz, 2H), 3.57 (br d, J=12.0 Hz, 1H), 3.40 (m, 1H), 2.90 (m, 1H), 2.29 (br d, J=14 Hz, 2H), 2.15 (m, 2H), 1.99 (m, 1H), 1.45 (m, 2H), 0.84 (br d, 2H). EM (calc.): 473.5; MS (ESI) m/e (M+1H)⁺: 474.2, (M−1H)⁻: 472.2

Compound 38: N-hydroxy-4-{3-[5-(tetrahydropyran-4-ylmethyloxy)benzofuran-2-ylcarbonyl-amino]prop-1-ynyl}benzamide.

¹H NMR (400 MHz, DMSO-$d_6$) δ 11.29 (s, 1H), 8.96 (t, J=5.6 Hz, 1H), 8.92 (br s, 1H), 7.75 (d, J=8.4 Hz, 2H), 7.51 (d, J=8.4 Hz, 2H), 7.44 (d, J=8.4 Hz, 1H), 6.96 (s, 1H), 6.90 (d, J=2.3 Hz, 1H), 9.81 (dd, $J_1$=2.3 Hz, $J_2$=8.9 Hz, 1H), 4.46 (d, J=7.1 Hz, 2H), 4.34 (d, J=5.6 Hz, 2H), 3.77 (dt, $J_1$=11.0 Hz, $J_2$=3.2 Hz, 2H), 3.14 (m, 2H), 1.99 (m, 1H), 1.29 (m, 4H). EM (calc.): 447.5; MS (ESI) m/e (M+1H)⁺: 448.5, (M−1H)⁻: 446.4.

Compound 39: N-hydroxy-4-{3-[5-(2-morpholin-4-yl-ethyloxy)benzofuran-2-ylcarbonyl-amino]prop-1-ynyl}benzamide hydrochloride.

$^1$H NMR (400 MHz, DMSO-d$_6$) δ 11.29 (s, 1H), 9.30 (t, J=6.0 Hz, 1 H), 7.74 (d, J=8.4 Hz, 2H), 7.63 (d, J=9.6 Hz, 1H), 7.58 (d, J=8.8 Hz, 1H), 7.50 (d, J=8.8 Hz, 2H), 7.39 (d, J=2.4 Hz, 1H), 7.15 (dd, J$_1$=9.2 Hz, J$_2$=2.8 Hz, 1H), 4.43 (s, 2H), 4.35 (d, J=5.6 Hz, 2H), 3.99 (d, J=10.8 Hz, 2H), 3.75 (t, J=10.8 Hz, 2H), 3.60 (d, J=4.0 Hz, 2H), 3.53 (d, J=14.4 Hz, 2H), 3.21 (d, J=11.2 Hz, 2H). EM (calc): 463.17; MS (ESI) m/e (M+1H)$^+$: 464.2, (M−1H)$^-$: 462.1.

Table II:

Compound 1: N-hydroxy-4-{3-[3-(4-chlorophenyl)ureido]prop-1-ynyl}benzamide.

$^1$H NMR (400 MHz, DMSO-d$_6$):δ 11.29 (s, 1H), 9.10 (s, 1H), 8.81 (s, 1H), 7.74 (d, J=8.1 Hz, 2H), 7.50 (d, J=8.5 Hz, 2H), 7.46 (d, J=8.8 Hz, 2H), 7.29 (d, J=9.1 Hz, 2H), 6.67 (t, J=5.6 Hz, 1H), 4.19 (d, J=6.0 Hz, 2H). EM (calc.): 343.1; MS (ESI) m/e (M+1H)$^+$: 343.9, (M−1H)$^-$: 342.1

Compound 2: N-hydroxy-4-{3-[3-(4-trifluoromethylphenyl)ureido]prop-1-ynyl}-benzamide.

$^1$H NMR (400 MHz, DMSO-d$_6$):δ 11.29 (s, 1H), 9.12 (s, 1H), 7.75 (d, J=8.2 Hz, 2H), 7.62 (m, J=8.9 Hz, 4H), 7.51 (d, J=8.2 Hz, 2H), 6.80 (t, J=5.8 Hz, 1H), 4.21 (d, J=5.4 Hz, 2H). EM (calc.): 377.1; MS (ESI) m/e (M+1H)$^+$: 378.0, (M−1H)$^-$: 376.0.

Compound 3: N-hydroxy-4-{3-[3-(phenyl)ureido]prop-1-ynyl}benzamide.

$^1$H NMR (400 MHz, DMSO-d$_6$):δ 11.25 (s, 1H), 9.06 (s, 1H), 8.61 (s, 1H), 7.71 (d, J=8.4 Hz, 2H), 7.47 (d, J=8.2 Hz, 2H), 7.38 (d, J=8.7 Hz, 2H), 7.21 (t, J=8.2 Hz, 2H), 6.89 (t, J=7.3 Hz, 1H), 6.56 (t, J=5.9 Hz, 1H), 4.16 (d, J=5.4 Hz, 2H). EM (calc.): 309.1; MS (ESI) m/e (M+1H)$^+$: 310.2, (M−1H)$^-$: 308.2.

Compound 4: N-hydroxy-4-{3-[3-(2-trifluoromethoxyphenyl)ureido]prop-1-ynyl}-benzamide.

$^1$H NMR (400 MHz, DMSO-d$_6$):δ 11.29 (s, 1H), 9.11 (s, 1H), 8.35 (s, 1H), 8.26 (dd, J$_1$=1.5 Hz, J$_2$=8.6 Hz, 1H), 7.75 (d, J=8.2 Hz, 2H), 7.52 (d, J=8.2 Hz, 2H), 7.33 (m, 3H), 7.05 (td, J$_1$=8.2 Hz, J$_2$=1.5 Hz, 1H), 4.24 (d, J=5.5 Hz, 2H). EM (calc.): 393.1; MS (ESI) m/e (M+1H)$^+$: 394.1, (M−1H)$^-$: 392.3.

Compound 5: N-hydroxy-4-[3-(phenylsulfonylamino)prop-1-ynyl]-benzamide.

$^1$H NMR (400 MHz, DMSO-d$_6$):δ 11.27 (s, 1H), 8.29 (t, J=5.3 Hz, 1H), 7.88 (dd, J$_1$=1.8 Hz, J$_2$=7.9 Hz, 2H), 7.68 (d, J=8.4 Hz, 2H), 7.64-7.57 (m, 3H), 7.19 (d, J=8.4 Hz, 2H), 4.05 (d, J=5.9 Hz, 2H). EM (calc.): 330.1; MS (ESI) m/e (M+1H)$^+$: 331.1, (M−1H)$^-$: 328.9.

Table III:

Compound 1: N-hydroxy-4-[3-methyl-3-(3-phenylacryloylamino)but-1-ynyl]-benzamide.

$^1$H NMR (400 MHz, DMSO-d$_6$):δ 11.29 (s, 1H), 8.34 (s, 1H), 7.75 (d, J=8.2 Hz, 2H), 7.57 (d, J=6.5 Hz, 2H), 7.46 (d, J=8.2 Hz, 2H), 7.43-7.40 (m, 3H), 6.72 (d, J=15.5 Hz, 1H), 1.70 (s, 6H). EM (calc.): 348.2; MS (ESI) m/e (M+1H)$^+$: 348.9, (M−1H)$^-$: 347.0.

Compound 2: N-hydroxy-4-[3-methyl-3-(4-phenylthiazol-2-ylcarbonylamino)but-1-ynyl]-benzamide.

$^1$H NMR (400 MHz, DMSO-d$_6$):δ 11.29 (s, 1H), 8.64 (s, 1H), 8.45 (s, 1H), 8.13 (d, J=7.0 Hz, 2H), 7.75 (d, J=8.2 Hz, 2H), 7.47-7.52 (m, 4H), 7.41 (m, 1H), 1.82 (s, 6H). EM (calc.): 405.1; MS (ESI) m/e (M+1H)$^+$: 406.1, (M−1H)$^-$: 404.2.

Compound 3: N-hydroxy-4-[3-methyl-3-(benzthiazol-2-ylcarbonylamino)but-1-ynyl]-benzamide.

$^1$H NMR (400 MHz, DMSO-d$_6$):δ 11.29 (s, I1H), 9.08 (s, 1H), 8.71 (s, 1H), 8.23 (s, 1H), 8.04 (dd, J$_1$=5.8 Hz, J$_2$=1.9 Hz, 1H), 7.96 (dd, J$_1$=7.1 Hz, J$_2$=1.9 Hz, 2H), 7.75 (d, J=8.5 Hz, 2H), 7.50-7.43 (m, 4H), 1.77 (s, 6H). EM (calc.): 378.1; MS (ESI) m/e (M+1H)$^+$: 378.9, (M−1H)$^-$: 377.0.

Compound 4: N-hydroxy-4-[3-methyl-3-(benzofuran-2-ylcarbonylamino)but-1-ynyl]-benzamide.

$^1$H NMR (400 MHz, DMSO-d$_6$) δ 11.23 (s, 1H), 9.02 (s, 1H), 8.56 (s, 1H), 7.74 (d, J=8.5 Hz, 1H), 7.68 (d, J=8.4 Hz, 2H), 7.62 (d, J=8.4 Hz, 1H), 7.58 (s, 1H), 7.43 (t, J=8.4 Hz, 1H), 7.40 (d, J=8.4 Hz, 2H), 7.29 (t, J=7.8 Hz, 1H), 1.71 (s, 6H). EM (calc.): 362.1; MS (ESI) m/e (M+1H)$^+$: 363.4, (M−1H)$^-$: 361.0.

Compound 5: N-hydroxy-4-[1-(benzofuran-2-yl-carbonylamino)-cycloprop-1-yl-ethynyl]-benzamide.

$^1$H NMR (400 MHz, DMSO-d$_6$) δ 11.24 (br s, 1H), 9.45 (s, 1H), 9.05 (br s, 1H), 7.76 (d, J=7.5 Hz, 1H), 7.69 (d, J=8.4 Hz, 2H), 7.64 (d, J=8.3 Hz, 1H), 7.60 (s, 1H), 7.45 (td, J$_1$=1.3 Hz, J$_2$=7.3 Hz, 1H), 7.42 (d, J=2H), 7.32 (t, J=7.9 Hz, 1H), 1.35 (m, 2H), 1.29 (m, 2H). EM (calc.): 360.1; MS (ESI) m/e (M+1H)$^+$: 361.3, (M−1H)$^-$: 359.1.

Compound 6: N-hydroxy-4-[1-(1H-indol-2-yl-carbonylamino)-cycloprop-1-yl-ethynyl]-benzamide.

$^1$H NMR (400 MHz, DMSO-d$_6$) δ 11.57 (s, 1H), 11.23 (s, 1H), 9.15 (s, 1H), 7.68 (d, J=8.4 Hz, 2H), 7.58 (d, J=7.9 Hz, 1H), 7.41 (dd, J$_1$=1.9 Hz, J=8.4 Hz, 3H), 7.16 (td, J$_1$=1.0 Hz, J$_2$=6.9 Hz, 1H), 7.11 (d, J=1.6 Hz, 1H), 7.01 (td, J$_1$=0.9 Hz, J$_2$=7.1 Hz, 1H), 1.37 (pseudo q, J=5.8 Hz, 2H), 1.26 (pseudo q, J=4.3 Hz, 2H). EM (calc.): 359.1; MS (ESI) m/e (M+1H)$^+$: 360.0, (M−1H)$^-$: 358.1.

Compound 7: N-hydroxy-4-[1-(benzofuran-2-ylcarbonylamino)-cyclobut-1-yl-ethynyl]-benzamide.

$^1$H NMR (400 MHz, DMSO-d$_6$) δ 11.25 (s, 1H), 9.27 (s, 1H), 7.77 (d, J=7.7 Hz, 11H), 7.71 (d, J=8.4 Hz, 2H), 7.65 (d, J=8.3 Hz, 1H), 7.58 (s, 1H), 7.46 (m, I1H), 7.45 (d, J=8.4 Hz, 2H), 7.32 (t, J=7.9 Hz, 1H), 2.58 (m, 4H), 2.01 (m, 2H). EM (calc.): 374.1; MS (ESI) m/e (M+1H)$^+$: 375.0, (M−1H)$^-$: 373.2.

Compound 8: N-hydroxy-4-[1-(benzofuran-2-ylcarbonylamino)-cyclohept-1-yl-ethynyl]-benzamide.

$^1$H NMR (400 MHz, DMSO-d$_6$) δ 11.24 (s, 1H), 9.03 (s, 1H), 8.74 (s, 1H), 7.76 (d, J=7.8, 1H), 7.69 (d, J=8.3 Hz, 2H), 7.65 (d, J=8.2 Hz, 1H), 7.60 (s, 1H), 7.45 (td, J$_1$=1.3 Hz, J$_2$=7.4 Hz, 1H), 7.41 (d, J=8.3 Hz, 2H), 7.32 (t, J=7.9 Hz, 1H), 2.35 (m, 1H), 2.20 (m, 2H), 1.78 (m, 4H). EM (calc.): 388.1; MS (ESI) m/e (M+1H)$^+$: 389.1, (M−1H)$^-$: 387.2.

Compound 9: N-hydroxy-4-[1-(benzofuran-2-yl-carbonylamino)-cyclohex-1-yl-ethynyl]-benzamide.

$^1$H NMR (400 MHz, DMSO-d$_6$) δ 11.25 (s, 1H), 9.10 (br s, 1H), 8.41 (s, 1H), 7.76 (d, J=7.7 Hz, 1H), 7.71 (d, J=8.3 Hz, 2H), 7.65 (d, J=8.3 Hz, I1H), 7.61 (s, 1H), 7.45 (td, J$_1$=1.3 Hz, J$_2$=7.2 Hz, 1H), 7.44 (d, J=8.3 Hz, 2H), 7.32, (td, J$_1$=0.7 Hz, J$_2$=7.8 Hz, 1H), 2.30 (m, 2H), 1.90 (m, 2H), 1.62 (m, 6H), 1.31 (m, 1H). EM (calc.): 402.2; MS (ESI) m/e (M+1H)$^+$: 403.3, (M−1H)$^-$: 401.3.

Compound 10: N-hydroxy-4-[1-(1H-indol-2-ylcarbonylamino)-cyclohex-1-yl-ethynyl]-benzamide.

$^1$H NMR (400 MHz, DMSO-d$_6$) δ 11.55 (s, 1H), 11.25 (s, 1H), 8.16 (s, 1H), 7.71 (d, J=8.3 Hz, 2H), 7.60 (d, J=8.0 Hz, 1H), 7.44 (d, J=8.3 Hz, 2H), 7.40 (d, J=8.8 Hz, 1H), 7.23 (d, J=1.9 Hz, 1H), 7.16 (pseudo td, J$_1$=1.1 Hz, J$_2$=7.1 Hz, 1H), 7.02 (pseudo td, J$_1$=0.7 Hz, J$_2$=7.8 Hz, 1H), 2.31 (m, 2H), 1.90 (m, 2H), 1.67 (m, 4H), 1.60 (m, 1H), 1.30 (m, 1H). EM (calc.): 401.2; MS (ESI) m/e (M+1H)$^+$: 402.4, (M−1H)$^-$: 400.4.

Compound 11: N-hydroxy-4-[1-(benzofuran-2-yl-carbonylamino)-cyclohept-1-yl-ethynyl]-benzamide.

$^1$H NMR (400 MHz, DMSO-d$_6$) δ 11.29 (s, 1H), 9.08 (s, 1H), 8.37 (s, 1H), 7.77 (d, J=7.7 Hz, 1H), 7.75 (d, J=8.3 Hz, 2H), 7.69 (d, J=8.4 Hz, 1H), 7.64 (s, 1H), 7.47 (t, J=7.2 Hz, 1H), 7.46 (d, J=8.4 Hz, 2H), 7.35 (t, J=7.7 Hz, 1H), 2.34 (m, 2H), 2.23 (m, 2H), 1.66 (m, 6H). EM (calc.): 416.5; MS (ESI) m/e (M+1H)$^+$: 417.0, (M−1H)$^-$: 415.4.

Compound 12: N-hydroxy-4-[1-(1H-indol-2-yl-carbonylamino)-cyclohept-1-yl-ethynyl]-benzamide.

$^1$H NMR (400 MHz, DMSO-d$_6$) δ 11.57 (s, 1H), 11.28 (s, 1H), 9.09 (br s, 1H), 8.12 (s, 1H), 7.74 (d, J=8.4 Hz, 2H), 7.63 (d, J=7.9 Hz, 1H), 7.45 (d, J=8.4 Hz, 2H), 7.41 (d, J=8.1 Hz, 1H), 7.26 (s, 1H), 7.20 (t, J=7.2 Hz, 1H), 7.05 (t, J=8.0 Hz, 1H), 2.35 (m, 2H), 2.23 (m, 2H), 1.67 (m, 8H). EM (calc.): 415.5; MS (ESI) m/e (M+1H)$^+$: 416.0, (M−1H)$^-$: 414.2.

Compound 13: N-hydroxy-4-[1-(1H-indol-2-yl-carbonylamino)-cyclopent-1-yl-ethynyl]-benzamide.

$^1$H NMR (400 MHz, DMSO-d$_6$) δ 11.57 (s, 1H), 11.27 (s, 1H), 9.07 (s, 1H), 8.46 (s, 1H), 7.73 (d, J=8.4 Hz, 2H), 7.63 (d, J=7.8 Hz, 1H), 7.44 (d, J=8.5 Hz, 2H), 7.24 (s, 1H), 7.20 (t, J=7.1 Hz, 1H), 7.05 (t, J=7.9 Hz, 1H), 2.26 (m, 2H), 2.24 (m, 2H), 1.84 (m, 4H). EM (calc.): 387.4; MS (ESI) m/e (M+1H)$^+$: 388.1, (M−1H)$^-$: 386.3.

Compound 14: N-hydroxy-4-[1-(1H-indol-2-yl-carbonylamino)-cyclobut-1-yl-ethynyl]-benzamide.

$^1$H NMR (400 MHz, DMSO-d$_6$) δ 11.56 (s, 1H), 11.28 (s, 1H), 9.08 (br s 1H), 8.96 (s, 1H), 7.74 (d, J=8.4 Hz, 2H), 7.64 (d, J=7.9 Hz, 1H), 7.48 (d, J=8.3 Hz, 2H), 7.44 (d, J=8.2 Hz, 1H), 7.22 (s, 1H), 7.20 (t, J=8.2 Hz, 1H), 7.06 (t, J=8.0 Hz, 1H), 2.62 (pseudo t, J=7.6 Hz, 4H), 2.08 (m, 2H). EM (calc.): 373.4; MS (ESI) m/e (M+1H)$^+$: 374.2, (M−1H)$^-$: 372.0.

Compound 15: N-hydroxy-4-[1-(benzothiophen-2-yl-carbonylamino)-cycloprop-1-yl-ethynyl]-benzamide.

$^1$H NMR (400 MHz, DMSO-d$_6$) δ 11.28 (s, 1H), 9.49 (s, 1H), 9.07 (s, 1H), 8.11 (s, 1H), 8.04 (d, J=7.2 Hz, 1H), 7.96 (d, J=9.0 Hz, 1H), 7.43 (d, J=8.3 Hz, 2H), 7.5 (pseudo t, J=8.0 Hz), 7.47 (m, 2H), 7.46 (d, J=7.1 Hz, 2H), 1.42 (pseudo q, J=5.9 Hz, 2H), 1.32 (pseudo q, J=4.1 Hz, 2H). EM (calc.): 376.4; MS (ESI) m/e (M+1H)$^+$: 376.9, (M−1H)$^-$: 375.2.

Compound 16: N-hydroxy-4-[4-(1H-indol-2-yl-carbonylamino)tetrahydrofuran-4-yl-ethynyl]-benzamide.

$^1$H NMR (400 MHz, DMSO-d$_6$) δ 11.61 (s, 1H), 11.30 (s, 1H), 9.12 (br s, 1H), 8.43 (s, 1H), 7.76 (d, J=8.4 Hz, 2H), 7.64 (d, J=7.9 Hz, 1H), 7.51 (d, J=8.4 Hz, 2H), 7.44 (d, J=8.2 Hz, 1H), 7.28 (s, 1H), 7.20 (t, J=7.1 Hz, 1H), 7.06 (t, J=7.1 Hz, 1H), 3.87 (m, 2H), 3.76 (pseudo t, J=9.9 Hz, 2), 2.35 (pseudo d, J=13.5 Hz, 2H), 2.13 (pseudo t, J=13.5 Hz, 2H). EM (calc.): 403.4; MS (ESI) m/e (M+1H)$^+$: 404.3, (M−1H)$^-$: 402.2.

Compound 17: N-hydroxy-4-[1-(4-methoxyindol-2-yl-carbonylamino)-cycloprop-1-yl-ethynyl]-benzamide.

$^1$H NMR (400 MHz, DMSO-d$_6$) δ 11.61 (s, 1H), 11.26 (s, 1H), 9.09 (s, 1H), 7.72 (d, J=8.4 Hz, 2H), 7.44 (d, J=8.4 Hz, 2H), 7.22 (s, 1H), 7.11 (t, J=7.9 Hz, 1H), 6.52 (d, J=8.3 Hz, 1H), 6.52 (d, J=7.7 Hz, 1H), 3.90 (s, 3H), 1.39 (pseudo q, J=2.7 Hz, 2H), 1.28 (pseudo q, J=2.7 Hz, 2H). EM (calc.): 389.4; MS (ESI) m/e (M+1H)$^+$: 390.3, (M−1H)$^-$: 388.3.

Compound 18: N-hydroxy-4-[1-(5-methoxyindol-2-yl-carbonylamino)-cycloprop-1-yl-ethynyl]-benzamide.

$^1$H NMR (400 MHz, DMSO-d$_6$) δ 11.45 (s, 1H), 11.27 (s, 1H), 9.14 (s, 1H), 9.07 (s, 1H), 7.72 (d, J=8.4 Hz, 2H), 7.45 (d, J=8.2 Hz, 2H), 7.34 (d, J=8.8 Hz, 1H), 7.07 (dd, J$_1$=2.4 Hz, J$_2$=11.2 Hz, 2H), 6.85 (dd, J$_1$=2.4 Hz, J$_2$=8.9 Hz, 1H), 3.78 (s, 3H), 1.40 (pseudo q, J=2.6 Hz, 2H),1.29 (pseudo q, J=2.6 Hz, 2H). EM (calc.): 389.4; MS (ESI) m/e (M+1H)$^+$: 390.2, (M−1H)$^-$: 388.3.

Compound 19: N-hydroxy-4-[4-(1H-indol-2-yl-carbonylamino)piperidin-4-yl-ethynyl]-benzamide.

$^1$H NMR (400 MHz, DMSO-d$_6$) δ 11.68 (s, 1H), 11.31 (s, 1H), 9.10 (s, 1H), 8.67 (br s, 2H), 8.61 (s, 1H), 7.77 (d, J=8.3 Hz, 2H), 7.64 (d, J=8.0 Hz, 1H), 7.54 (d, J=8.3 Hz, 2H), 7.44 (d, J=8.2 Hz, 1H), 7.30 (s, 1H), 7.22 (t, J=7.0 Hz, 1H), 7.07 (t, J=7.8 Hz, 1H), 3.36 (m, 2H), 3.24 (m, 2H), 2.54 (br m, 2H), 2.36 (m, 2H). EM (calc.): 402.5; MS (ESI) m/e (M+1H)$^+$: 403.0, (M−1H)$^-$: 400.8.

Compound 20: N-hydroxy-4-[4-(benzofuran-2-yl-carbonylamino)piperidin-4-yl-ethynyl]-benzamide hydrochloride.

$^1$H NMR (400 MHz, DMSO-dr) δ 11.32 (s, 1H), 9.11 (s, 1H), 8.94 (s, 1H), 8.67 (br s, 2H), 7.82 (d, J=7.3 Hz, 1H), 7.78 (d, J=8.4 Hz, 2H), 7.71 (s, 1H), 7.70 (d, J=7.0 Hz, 1H), 7.55 (d, J=8.3 Hz, 2H), 7.51 (t, J=7.4 Hz, 1H), 7.37 (t, J=7.9 Hz, 1H), 3.36 (m, 2H), 3.23 (m, 2H), 2.53 (m, 2H), 2.37 (m, 2H). EM (calc.): 403.4; MS (ESI) m/e (M+1H)$^+$: 404.3, (M−1H)$^-$: 402.1.

Compound 21: N-hydroxy-4-[4-(1H-indol-2-yl-carbonylamino)-1-(2,2,2-trifluoroethyl)-piperidin4-yl-ethynyl]-benzamide.

$^1$H NMR (400 MHz, DMSO-d$_6$) δ 11.65 (s, 1H), 11.30 (br s, 1H), 8.47 (s, 1H), 7.76 (d, J=8.3 Hz, 2H), 7.64 (d, J=7.9 Hz, 1H), 7.50 (d, J=8.2 Hz, 2H), 7.44 (d, J=8.0 Hz, 1H), 7.28 (s, 1H), 7.20 (t, J=7.8 Hz, 1H), 7.06 (t, J=7.4 Hz, 1H), 3.66 (br s, 1H), 3.10 (m, 3H), 2.44 (m, 2H), 2.34 (m, 2H). EM (calc.): 484.5; MS (ESI) m/e (M+1H)$^+$: 485.4, (M−1H)$^-$: 483.1.

Example 9

Synthesis of acetyl-Gly-Ala-(N-acetyl-Lys)-AMC tert-Boc (N-Acetyl-Lys)-AMC (445 mg, 1 mmol, purchased from Bachem) was dissolved in 4M HCl in dioxane to provide H-(N-acetyl-Lys)-AMC as a white solid. To a solution of H-(N-acetyl-Lys)-AMC in DMF (5 ml) was added Ac-Gly-Ala-OH (188 mg, 1.0 mmol) using PyBOP (520 mg, 1.0 mmol), HOBt-H$_2$O (135 mg, 1.0 mmol), and NMM (0.296 ml, 2.0 mmol). The reaction mixture was stirred for 1 h and monitored by MS/LC for the presence of H-(N-acetyl-Lys)-AMC. Additional amounts of PyBOP (260 mg, 0.5 mmol), HOBt-H$_2$O (70 mg, 0.5 mmol), and NMM (0.146 ml, 1.0 mmol) were added and the stirring was continued for additional 4 h after which the product was isolated in quantative yield.

Biological Examples

Example 1

Inhibition of HDAC in Vitro

The HDAC inhibitory activity of the compounds of this invention in vitro was determined as follows.

Measurements were performed in a reaction volume of 100 μL using 96-well assay plates. HDAC-1 (200 pM final concentration) in reaction buffer (50 mM HEPES, 100 mM KCl, 0.001% Tween-20, 5% DMSO, pH 7.4) was mixed with inhibitor at various concentrations and allowed to incubate for 30 min, after which trypsin and acetyl-Gly-Ala-(N-acetyl-Lys)-AMC were added to final concentrations of 50 nM and 25 µM, respectively, to initiate the reaction. Negative control reactions were performed in the absence of inhibitor in replicates of eight.

The reactions were monitored in a fluorescence plate reader. After a 30 min lag time, the fluorescence was measured over a 30 min time frame using an excitation wavelength of 355 nm and a detection wavelength of 460 nm. The increase in fluorescence with time was used as the measure of the reaction rate. Inhibition constants were obtained using the program BatchKi (Kuzmic et al. *Anal. Biochem.* 286, 45-50, (2000)). The $K_i$ for Compound 22, Table I, was 0.022 µm.

Example 2

Cell proliferation assay in Vitro

The ability of the compounds of Formula (I) to inhibit growth of tumor cells in vitro was determined as follows.

Stock cultures of the DU 145 prostate carcinoma cell line were maintained in RPMI medium 1640 containing 10% (v/v) fetal bovine serum, 2 mM L-glutamine, 1 mM sodium pyruvate, 50 units/ml penicillin, and 50 µg/ml streptomycin at 37° C. in 5% $CO_2$ humidified atmosphere. Cells were cultured in 75-cm$^2$ culture flasks and subcultures were established every 3 to 4 days so as not to allow the cells to exceed 90% confluence.

DU 145 cells were harvested for proliferation assays by trypsinization (0.05% trypsin/0.53 mM EDTA), washed twice in culture medium, resuspended in appropriate volume of medium, and then counted using a hemacytometer. Cells were seeded in wells of flat-bottom 96-well plates at a density of 5,000 cell/well in 100 µl. Cells were allowed to attach for 1.5 to 2 h at 37° C.

Compounds were diluted from 10 mM stock solutions in DMSO. Serial 3-fold dilutions were performed in medium containing 0.6% DMSO in wells (in triplicate) of a 96-well U-bottom plates starting with a 60 µM solution. After dilutions were completed, 100 µl of each compound dilution (in triplicate) was transferred to designated triplicate wells of the 96-well plate containing cells in 100 µl of medium. Final concentrations of the dose-response for compounds in assay plates ranged from 0.12 to 30 µM. Control wells (cells with no treatment) received 100 µl of 0.6% DMSO in culture medium. Wells containing medium with no cells served as the background wells. Cells were cultured with the compounds for 48 and 72 h at 37° C. in a humidified $CO_2$ incubator.

Cell proliferation was assessed by measuring fluorescence after the addition of the fluorogenic redox indicator, Alamar Blue™ (BioSource International). Ten µl of Alamar Blue™ was added to each well of the 96-well plate(s) 3 to 4 h prior to the end of the incubation period. Assay plates were read in a fluorescence plate reader (excitation, 530 nm; emission, 620 nm). $GI_{50}$ values (concentration at which the growth of the tumor cells was inhibited by 50%) for compounds were determined by plotting the percent control fluorescence against the logarithm of the compound concentration. The compounds of this invention inhibited the growth of the tumor cells.

Pharmaceutical Composition Examples

The following are representative pharmaceutical formulations containing a compound of Formula (I)

Tablet Formulation

The following ingredients are mixed intimately and pressed into single scored tablets

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 1.2 g |
| sodium acetate buffer solution, | 0.4M 2.0 ml |

-continued

| Ingredient | Amount |
| --- | --- |
| HCl (1N) or NaOH (1N) | q.s. to suitable pH |
| water (distilled, sterile) | q.s. to 20 ml |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol™ H-15 (triglycerides of saturated vegetable fatty acid; Riches-Nelson, Inc., New York), and has the following composition:

| compound of the invention | 500 mg |
| --- | --- |
| Witepsol ™ H-15 | balance |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

I claim:
1. A compound of Formula (I):

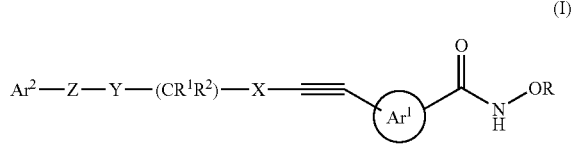

(I)

wherein:
R is hydrogen;
Ar¹ is phenylene and the triple bond attached to Ar¹ is in the para position relative to the —CONHOH group, wherein said Ar¹ is optionally substituted with one or two substituents independently selected from alkyl, halo, alkoxy, haloalkoxy, or haloalkyl;
X and Y are a bond;
R¹ and R² are hydrogen or alkyl;
Z is —CONH—;
Ar² is heteroaryl;
and individual stereoisomers, individual geometric isomers, or mixtures thereof; or a pharmaceutically acceptable salt thereof.

2. The compound of claim 1 wherein Ar² is thiophenyl, pyridinyl, quinolinyl, thiazolyl, benzthiazolyl, benzoxazolyl, furanyl, benzimidazolyl, benzothiophenyl, pyrrolyl, indolyl, isoindolyl, or isoquinolinyl optionally substituted with one or two substituents independently selected from alkyl, alkoxy, alkoxyalkyl, halo, haloalkyl, haloalkoxy, alkylamino, dialkylamino, hydroxy, hydroxyalkyl, hydroxyalkyloxy, aminoalkyl, aminoalkoxy, alkoxyalkyloxy, optionally substituted phenyl, optionally substituted heteroaryl, optionally substituted phenyloxyalkyl, optionally substituted heteroaralkyloxy, optionally substituted heteroaryloxyalkyl, optionally substituted heterocycloalkylalkyloxy, or optionally substituted heterocycloalkylalkyl.

3. The compound of claim 1 wherein Ar² is thiazolyl, quinolinyl, oxazulyl, benzothiophenyl, indolyl, benzofuranyl, benzthiazolyl, or benzimidazolyl optionally substituted with a substituent selected from halo, haloalkyl, alkoxy, haloalkoxyalkyl, aminoalkoxy, aminoalkyl, alkoxyalkyloxy, alkoxyalkyloxyalkyl, optionally substituted heterocycloalkyloxy, optionally substituted hetrocycloalkylalkyloxy, or phenyl optionally substituted with -(alkylene)NRR' where R and R' are independently hydrogen or alkyl.

4. A compound selected from the group consisting of:
N-hydroxy-4-[3-(3-phenylacryloylamino)prop-1-ynyl]-benzamide,
N-hydroxy-4-[3-(4-phenylthiazol-2-ylcarbonylamino)prop-1-ynyl]-benzamide;
N-hydroxy-4-[3-S-(3-phenylacryloylamino)-but-1-ynyl]-benzamide;
N-hydroxy-4-[3-(4-methoxyquinolin-2-ylcarbonylamino)prop-ynyl]-benzamide;
N-hydroxy-4-{3-[2-(4-aminomethylphenyl)oxazol-5-ylcarbonylamino}prop-1-ynyl]-benzamide hydrochloride;
N-hydroxy-4-[3S-(4-phenylthiazol-2-ylcarbonylamino)but-1-ynyl]-benzamide;
N-hydroxy-4-[3-(phenylcarbonlamino)prop-1-ynyl[-benzamide;
N-hydroxy-4-[3-(benzothiophen-2-ylcarbonylamino)prop-1-ynyl]-benzamide;
N-hydroxy-4-[3-(5-chlorobenzofuran-2-ylcarbonylamino)-prop-1-ynyl]-benzamide;
N-hydroxy-4-[3-(5-indol-2-ylcarbonylamino)prop-1-ynyl]-benzamide;
N-hydroxy-4-[3-(benzofuran-2-ylcarbonylamino)prop-1-ynyl]-benzarmide;
N-hydroxy-4-[3S-(benzothiophen-2-ylcarbonylamino)but-1-ynyl]-benzamide;
N-hydroxy-4-[3-(indol-2-ylcarbonylamino)prop-1-ynyl]-benzamide;
N-hydroxy-4-{3-[3-(2,2,2-trifluoroethyloxymethyl)benzofuran-2-yl-carbonyl-amino]prop-1-vnyl }-benzamide;
N-hydroxy-4-[3-(benzthiazol-2-ylcarbonylamino)prop-1-ynyl]-benzamide;
N-hydroxy-4-[3-(4-trifluoromethylbenzothiophen-2-yl-carbonyl-amino)prop-1-ynyl]-benzamide;
N-hydroxy-4-[3-(5-fluorobenzothiophen-2-ylcarbonylamino)prop-1-ynyl]-benzamide;
N-hydroxy-4-[3-(3-N,N-dimethylaminomethylbenzofuran-2-ylcarbonylamino)prop-1-ynyl]-benzamide hydrochloride;
N-hydroxy-4-{3-[1-(2-N,N-dimethylaminoethyl)benzimidazol-2-ylcarbonyl-amino]prop-1-ynyl}benzamide;
N-hydroxy-4-[3-(4-methoxybenzofuran-2-ylcarbonylamino)prop-1-ynyl]-benzamide;

N-hydroxy-4-[3-(4-N,N-dimethylaminoethoxybenzofuran-2-ylcazbonylamino-)prop-1-ynyl]-benzamide hydrochloride,
N-hydroxy-4-[3-(4-methoxyindol-2ylcarbonylamino)prop-1-ynyl]-benzamide;
N-hydroxy-4-[3-(4-N,N-dimethylaminoethoxyindol-2-yl-carbonylamino)prop-1-ynyl]-benzamide;
N-hydroxy-4-[3-(5-methoxyindol-2-ylcarbonylamino)prop-1-ynyl]-benzamide;
N-hydroxy-4-[3-(5-N,N-dimethylaminoethoxyindol-2-ylcarbonyl-amino)prop-1-ynyl]-benzamide hydrochloride;
N-hydroxy-4-{3-[3-(2-methoxyethyloxymethyl)-benzofuran-2-yl-carbonylamino]prop-1-ynyl]benzamide;
N-hydroxy-4-{3-[3-(2-methoxyethyloxy)indol-2-yl-carbonylamino]prop-1-ynyl}-benzamide;
N-hydroxy-4-[3-(5-tetrahydropyran-4-yloxybenzofuran-2-yl-carbonylamino)prop-1-ynyl]benzamide;
N-hydroxy-4-{3-[5-(2-pyrrolidin-1-ylethoxy)benzofuran-2-yl-carbonylamino]prop-1-ynyl}benzamide hydrochloride;
N-hydroxy-4-{3-[5-(2-methoxyethyloxy)benzofuran-2-yl-carbonylamino]prop-1-ynyl}-benzamide;
N-hydroxy-4-{3-[4-(N,N-dimethylaminoethyloxy)quinolin-2-yl-carbonylamino]prop-1-ynyl}benzamide hydrochloride;
N-hydroxy-4-{3-[5-(1-(2,2,2-trifluoroethyl)piperidin-4-yloxy)benzofuran-2-ylcarbonyl-amino ]prop-1-ynyl}benzamide;
N-hydroxy-4-{3-[5-(1-cyclopropylpiperidin-4-yloxy)benzofuran-2-yl-carbonylamino]-prop-1-ynyl}benzamide hydrochloride;
N-hydroxy-4-{3-[5-(tetrahydropyran-4-ylmethyloxy)benzofuran-2-ylcarbonylamino]-prop-1-ynyl}benzamide;
N-hydroxy-4-{3-[5-(2-morpholin-4-ylethyloxy)benzofuran-2-yl-carbonylamino]prop-1-ynyl}benzamide hydrochloride;
N-hydroxy-4-{3-[3-(4-chlorophenyl)ureido]prop-1-ynyl}benzamide;
N-hydroxy-4-{3-[3-(4-trifluorormethylphenyl)ureido]prop-1-ynyl}benzamide;
N-hydroxy-4-{3-[3-(phenyl)ureido]prop-1-ynyl}benzamide;
N-hydroxy-4-{3-[3-(2-trifluoromethyloxyphenyl)ureido]prop-1-ynyl}benzamide;
N-hydroxy-4-[3-methyl-3-(3-phenylacryloylamino)but-1-ynyl]-benzamide;
N-hydroxy-4-[3-methyl-3-(4-phenylthiazol-2-ylcarbonylamino)but-1-ynyl]-benzamide;
N-hydroxy-4-[3-methyl-3-(benzithiazol-2-ylcarbonylamino)but-1-ynyl]-benzamide; and
N-hydroxy-4-[3-methyl-3-(benzofuran-2-ylcarbonylamino)but-1-ynyl]-benzamide; or a pharmaceutically acceptable salt thereof.

5. N-hydroxy-4-[3-(5-N,N-dimethylaminoethoxyindol-2-ylcarbonylamino)prop-1-ynyl}-benzamide; or a pharmaceutically acceptable salt thereof and having the structure:

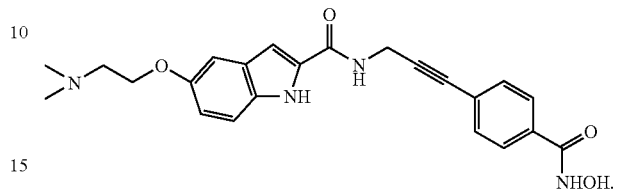

6. N-hydroxy-4-[3-(2-methoxyethyloxymethyl)indol-2-ylcarbonylamino)prop-1-ynyl]-benzamide; or a pharmaceutically acceptable salt thereof and having the structure:

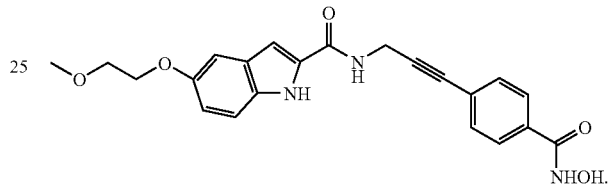

7. A pharmaceutical composition comprising a therapeutically effective amount of a compound of claim 1 and a pharmaceutically acceptable excipient.

8. A pharmaceutical composition comprising a therapeutically effective amount of a compound of claim 2 and a pharmaceutically acceptable excipient.

9. A pharmaceutical composition comprising a therapeutically effective amount of a compound of claim 3 and a pharmaceutically acceptable excipient.

10. A pharmaceutical composition comprising a therapeutically effective amount of a compound of claim 4 and a pharmaceutically acceptable excipient.

11. A pharmaceutical composition comprising a therapeutically effective amount of a compound of claim 5 and a pharmaceutically acceptable excipient.

12. A pharmaceutical composition comprising a therapeutically effective amount of a compound of claim 6 and a pharmaceutically acceptable excipient.

* * * * *